United States Patent [19]
Scherkenbeck et al.

[11] Patent Number: 5,663,140
[45] Date of Patent: Sep. 2, 1997

[54] USE OF CYCLIC DEPSIPEPTIDES HAVING 12 RING ATOMS FOR COMBATING ENDOPARASITES, NEW CYCLIC DESPIPEPTIDES HAVING 12 RING ATOMS, AND PROCESSES FOR THEIR PREPARATION

[75] Inventors: Jürgen Scherkenbeck, Wermelskirchen; Peter Jeschke, Leverkusen; Andrew Plant, Odenthal; Achim Harder, Köln; Norbert Mencke, Leverkusen, all of Germany

[73] Assignee: Bayer Aktiengesellschaft, Leverkusen, Germany

[21] Appl. No.: 372,543

[22] Filed: Jan. 13, 1995

[30] Foreign Application Priority Data

Jan. 19, 1994 [DE] Germany .................. 44 01 389.2

[51] Int. Cl.$^6$ .................. A61K 38/00; A61K 35/78; C07D 273/08
[52] U.S. Cl. .................. 514/11; 530/370; 540/454
[58] Field of Search .................. 514/11; 530/370; 540/454

[56] References Cited

U.S. PATENT DOCUMENTS 5,116,815  5/1992  Takagi et al. .................. 514/11

FOREIGN PATENT DOCUMENTS 0382173  8/1990  European Pat. Off. .
9325543  12/1993  WIPO .

OTHER PUBLICATIONS

U. Schmidt et al; Synthesis, pp. 294–300 (1991).
U. Schmidt et al; J. Org. Chem, vol. 47, pp. 3261–3262 (1982).
B.K. Varnstein et al; Kemiai Koezlemenyek, vol. 60, No. 10, pp. 10–25 (1983).
J. Konnert et al., J. Am. Chem. Soc, vol. 91, No. 17, pp. 4888–4892 (1969).

*Primary Examiner*—Jerry D. Johnson
*Attorney, Agent, or Firm*—Sprung Horn Kramer & Woods

[57] ABSTRACT

The present invention relates to the use of cyclic depsipeptides having 12 ring atoms of the general formula (I)

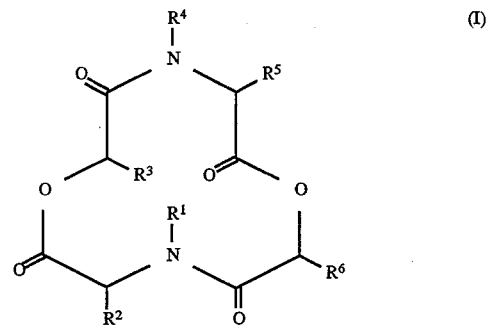

in which $R^1$ and $R^4$ independently of one another represent hydrogen, straight-chain or branched alkyl, cycloalkyl, aralkyl, aryl, heteroaryl or heteroarylalkyl, each of which is optionally substituted, $R^2$, $R^3$, $R^5$ and $R^6$ independently of one another represent hydrogen, straight-chain or branched alkyl having up to 8 carbon atoms, halogenoalkyl, hydroxyalkyl, alkanoyloxyalkyl, alkoxyalkyl, aryloxyalkyl, mercaptoalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, guanidinoalkyl which can optionally be substituted by one or two benzyloxycarbonyl radicals or by one, two, three or four alkyl radicals, alkoxycarbonylaminoalkyl, 9-fluorenylmethoxycarbonyl(Fmoc)aminoalkyl, alkenyl, cycloalkyl, cycloalkylalkyl, and optionally substituted aryl, arylalkyl, heteroaryl and heteroarylalkyl, and their optical isomers and racemates, in medicine and veterinary medicine for combating endoparasites, to new depsipeptides having 12 ring atoms, and to processes for their preparation.

17 Claims, No Drawings

USE OF CYCLIC DEPSIPEPTIDES HAVING 12 RING ATOMS FOR COMBATING ENDOPARASITES, NEW CYCLIC DESPIPEPTIDES HAVING 12 RING ATOMS, AND PROCESSES FOR THEIR PREPARATION

The present invention relates to the use of cyclic depsipeptides having 12 ring atoms for combating endoparasites, to new cyclic depsipeptides having 12 ring atoms, and to processes for their preparation.

Certain cyclic depsipeptides having 12 ring atoms and processes for their preparation are already known (cf. for example: J. Am. Chem. Soc. 91 (1969), p. 4888; Biorg. Khim. 1 (1975), 375; Biofizika 16 (1971) p. 407; Iav. Akad. Nark. SCSR, Set Khim, 1970, p. 991).

However, nothing has yet been disclosed about a use of these compounds against endoparasites.

The present invention relates to:

1. The use of cyclic depsipeptides having 12 ring atoms of the general formula (I)

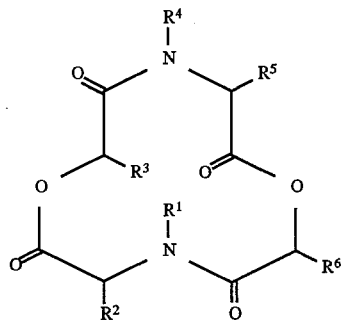

in which $R^1$ and $R^4$ independently of one another represent hydrogen, straight-chain or branched alkyl, cycloalkyl, aralkyl, aryl, heteroaryl, heteroarylalkyl, each of which is optionally substituted, $R^2$, $R^3$, $R^5$ and $R^6$ independently of one another represent hydrogen, straight-chain or branched alkyl having up to 8 carbon atoms, halogenoalkyl, hydroxyalkyl, alkanoyloxyalkyl, alkoxyalkyl, aryloxyalkyl, mercaptoalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, guanidinoalkyl which can optionally be substituted by one or two benzyloxycarbonyl radicals or by one, two, three or four alkyl radicals, alkoxycarbonylaminoalkyl, 9-fluorenylmethoxycarbonyl(Fmoc)aminoalkyl, alkenyl, cycloalkyl, cycloalkylalkyl, and optionally substituted aryl, arylalkyl, heteroaryl or heteroarylalkyl, and their optical isomers and racemates, in medicine and veterinary medicine for combating endoparasites.

2. New cyclic depsipeptides having 12 ring atoms of the formula (I)

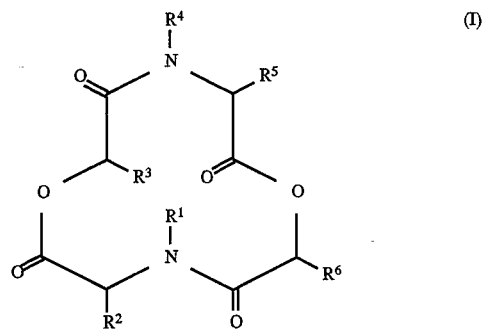

in which $R^1$ represents hydrogen, $C_{1-9}$-alkyl, $C_{3-6}$-cycloalkyl, $C_{1-8}$-halogenoalkyl, aralkyl, aryl, heteroaryl, heteroarylalkyl, each of which is optionally substituted, $R^2$ represents hydrogen, straight-chain or branched alkyl having up to 8 carbon atoms, halogenoalkyl, hydroxyalkyl, alkanoyloxyalkyl, alkoxyalkyl, aryloxyalkyl, mercaptoalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, guanidinoalkyl which can optionally be substituted by one or two benzyloxycarbonyl radicals or by one, two, three or four alkyl radicals, alkoxycarbonylaminoalkyl, 9-fluorenylmethoxycarbonyl(Fmoc)aminoalkyl, alkenyl, cycloalkyl, cycloalkylalkyl, and optionally substituted aryl, arylalkyl, heteroaryl or heteroarylalkyl, $R^3$ represents hydrogen, straight-chain or branched alkyl having up to 8 carbon atoms, halogenoalkyl, hydroxyalkyl, alkanoyloxyalkyl, alkoxyalkyl, aryloxyalkyl, mercaptoalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, guanidinoalkyl which can optionally be substituted by one or two benzyloxycarbonyl radicals or by one, two, three or four alkyl radicals, alkoxycarbonylaminoalkyl, 9-fluorenylmethoxycarbonyl(Fmoc)aminoalkyl, alkenyl, cycloalkyl, cycloalkylalkyl, and optionally substituted aryl, arylalkyl, heteroaryl or heteroarylalkyl, $R^4$ represents $C^{1-9}$-alkyl, $C_{3-6}$-cycloalkyl, $C_{1-8}$-halogenoalkyl, aralkyl, aryl, heteroaryl and heteroarylalkyl, each of which is optionally substituted, $R^5$ represents hydrogen, straight-chain or branched alkyl having up to 8 carbon atoms, halogenoalkyl, hydroxyalkyl, alkanoyloxyalkyl, alkoxyalkyl, aryloxyalkyl, mercaptoalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, guanidinoalkyl which can optionally be substituted by one or two benzyloxycarbonyl radicals or by one, two, three or four alkyl radicals, alkoxycarbonylaminoalkyl, 9-fluorenylmethoxycarbonyl(Fmoc)aminoalkyl, alkenyl, cycloalkyl, cycloalkylalkyl, and optionally substituted aryl, arylalkyl, heteroaryl or heteroarylalkyl, $R^6$ represents halogenoalkyl, hydroxyalkyl, alkanoyloxyalkyl, alkoxyalkyl, aryloxyalkyl, mercaptoalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, guanidinoalkyl which can optionally be substituted by one or two benzyloxycarbonyl radicals or by one, two, three or four alkyl radicals, alkoxycarbonylaminoalkyl, 9-fluorenylmethoxycarbonyl(Fmoc)aminoalkyl, alkenyl, cycloalkyl, cycloalkylalkyl, and optionally substituted aryl, arylalkyl, heteroaryl or heteroarylalkyl, with the proviso that, in the event that one of the radicals $R^1$ and $R^4$ represents a radical other than a methyl radical, the radical $R^6$ additionally to the abovementioned meanings can represent hydrogen or straight-chain or branched $C_{1-9}$-alkyl.

3. Process for the preparation of the new cyclic depsipeptides having 12 ring atoms of the formula (I) in accordance with item 2 (above)

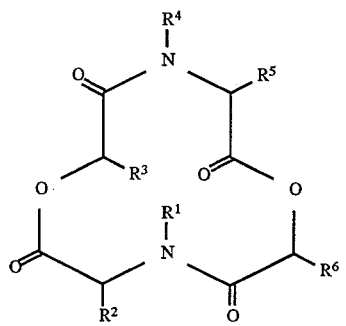

in which
the radicals $R^1$–$R^6$ have the meaning given under item 2, characterized in that open-chain tetradepsipeptides of the formula (II)

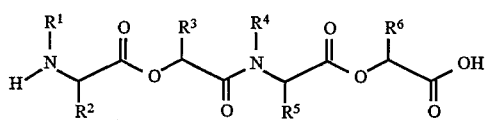

in which
$R^1$ to $R^6$ have the abovementioned meaning, are subjected to a cyclization reaction in the presence of a diluent and in the presence of a coupling reagent.

4. Open-chain tetradepsipeptides of the formula (II)

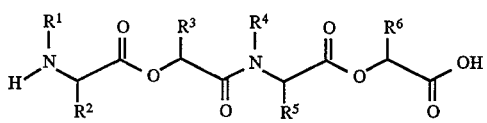

in which
$R^1$ to $R^6$ have the abovementioned meaning.

5. Process for the preparation of the open-chain tetradepsipeptides of the formula (II)

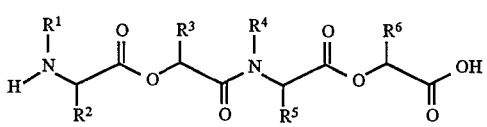

in which
$R^1$ to $R^6$ have the abovementioned meaning, characterized in that 1a) compounds of the formula (III)

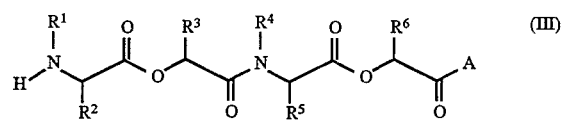

in which
A represents tert-butoxy and
$R^1$ to $R^6$ have the abovementioned meaning, are hydrolyzed in the presence of a diluent and of a protonic acid, or 1b) compounds of the formula (IV)

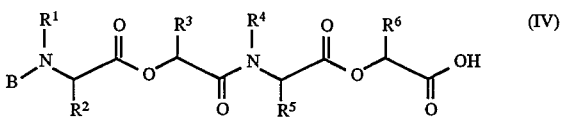

in which
B represents benzyl and
$R^1$ $R^6$ have the abovementioned meaning, are subjected to hydrogenolysis in the presence of a diluent and of a catalyst.

6. Compounds of the formula (III)

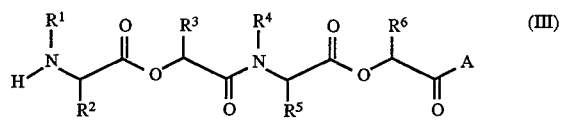

in which
A for tert-butoxy and
$R^1$ to $R^6$ have the abovementioned meaning.

7. Process for the preparation of the compounds of the formula (III)

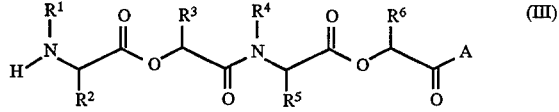

in which
A for tert-butoxy and
$R^1$ to $R^6$ have the abovementioned meaning, characterized in that compounds of the formula (V)

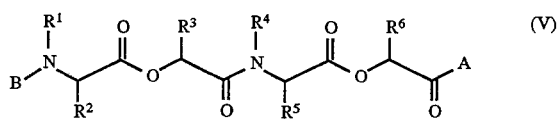

in which
A for tert-butoxy,
B for benzyl and
$R^1$ to $R^6$ have the abovementioned meaning, are subjected to hydrogenolisis in the presence of a diluent and of a catalyst.

8. Compounds of the formula (IV)

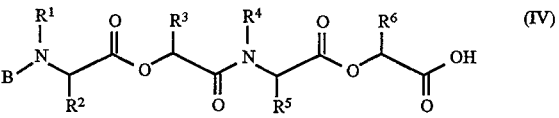

in which

B represents benzyl and

R¹ to R⁶ have the abovementioned meaning.

9. Process for the preparation of the compounds of the formula (IV)

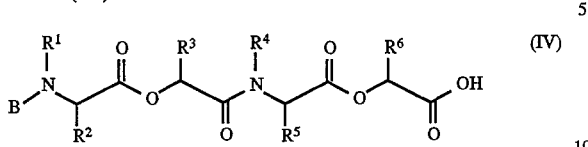

in which

B represents benzyl and

R¹ to R⁶ have the abovementioned meaning, characterized in that compounds of the formula (V)

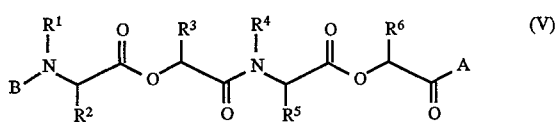

in which

B for benzyl,

A for tert-butoxy and

R¹ to R⁶ have the abovementioned meaning, are hydrolyzed in the presence of a diluent and of a protonic acid.

10. Compounds of the formula (V)

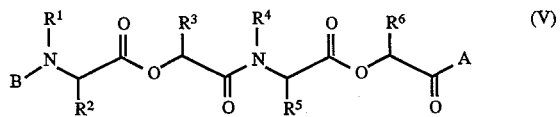

in which

B for benzyl,

A for tert-butoxy and

R¹ to R⁶ have the abovementioned meaning.

11. Process for the preparation of the compounds of the formula (V)

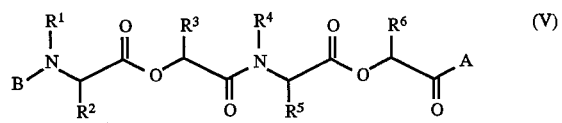

in which

A for tert-butoxy,

B for benzyl and

R¹ to R⁶ have the abovementioned meaning, characterized in that didepsipeptides of the formula (VI)

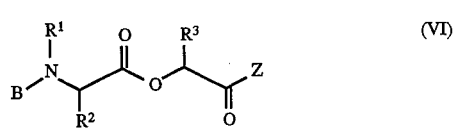

in which

B represents benzyl,

Z represents OH or Cl and

R¹ to R³ have the abovementioned meaning, and didepsipeptides of the formula (VII)

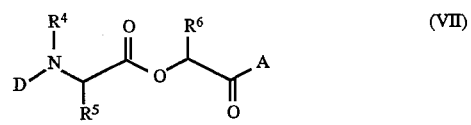

in which

D represents hydrogen and

A represents tert-butoxy, and

R⁴ to R⁶ have the abovementioned meaning, are subjected to a condensation reaction in the presence of a diluent and of a suitable coupling reagent.

12. Didepsipeptides of the formula (VI)

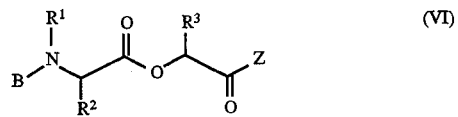

in which

B represents benzyl,

Z represents OH or Cl and

R¹ to R³ have the abovementioned meaning.

13. Process for the preparation of didepsipeptides of the formula (VI)

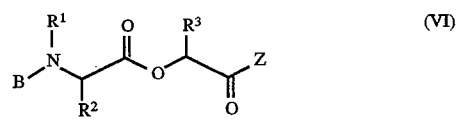

in which

B represents benzyl and

Z represents OH or Cl, and

R¹ to R³ have the abovementioned meaning, characterized in that a compound of the formula (VIII)

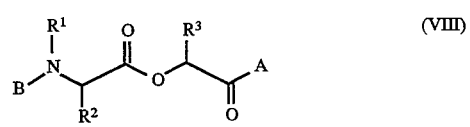

in which

A represents tert-butoxy and

B represents benzyl, and

R¹ to R³ have the abovementioned meaning, is hydrolyzed in the presence of a diluent and of a protonic acid.

14. Didepsipeptides of the formula (VIII)

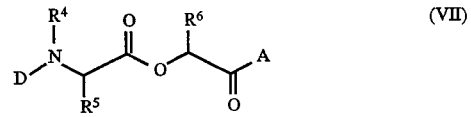

in which

D represents hydrogen and

A represents tert-butoxy, and

R⁴ to R⁶ have the abovementioned meaning.

15. Process for the preparation of didepsipeptides of the formula (VII)

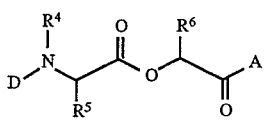 (VII)

in which

D represents hydrogen and

A represents tert-butoxy, and $R^4$ to $R^6$ have the abovementioned meaning, characterized in that compounds of the formula (IX)

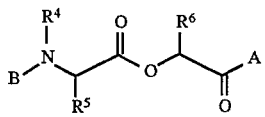 (IX)

in which

A represents tert-butoxy,

B represents benzyl and $R^4$ to $R^6$ have the abovementioned meaning, are subjected to hydrogenolysis in the presence of a diluent and of a catalyst.

16. Didepsipeptides of the formula (VIII)

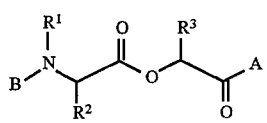 (VIII)

in which

A represents tert-butoxy and

B represents benzyl, and $R^1$ to $R^3$ have the abovementioned meaning.

17. Process for the preparation of didepsipeptides of the formula (VIII)

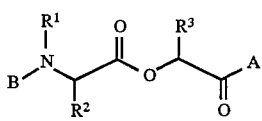 (VIII)

in which

A represents tert-butoxy and

B represents benzyl, and $R^1$ to $R^3$ have the abovementioned meaning, characterized in that an amino carboxylic acid of the formula (X)

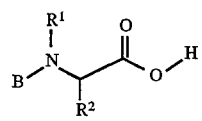 (X)

in which

B represents benzyl and $R^1$ and $R^2$ have the abovementioned meaning, in the form of its alkali metal salt, preferably its caesium salt, and an α-halogeno carboxylic acid of the formula (XI)

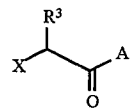 (XI)

in which

X represents Cl or Br and

A represents tert-butoxy and $R^3$ has the abovementioned meaning, are subjected to a coupling reaction in the presence of a diluent.

18. Didepsipeptides of the formula (IX)

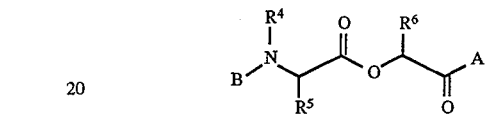 (IX)

in which

A represents tert-butoxy and

B for benzyl and $R^4$ to $R^6$ have the abovementioned meaning.

19. Process for the preparation of didepsipeptides of the formula (IX)

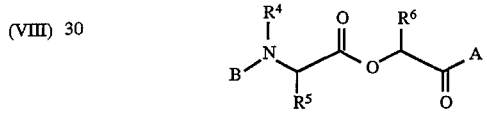 (IX)

in which

A represents tert-butoxy and

B for benzyl and $R^4$ to $R^6$ have the abovementioned meaning, characterized in that an amino carboxylic acid of the formula (XII)

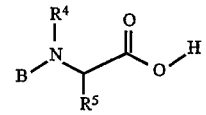 (XII)

in which

B represents benzyl and $R^4$ and $R^5$ have the abovementioned meaning, in the form of its alkali metal salt, preferably its caesium salt, is subjected to a coupling reaction with an α-halogeno carboxylic acid of the formula (XIII)

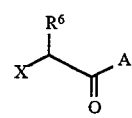 (VIII)

in which

X represents Cl or Br and

A represents tert-butoxy and $R^6$ has the abovementioned meaning, in the presence of a diluent.

The cyclic depsipeptides having 12 ring atoms of the formula (I) and their acid addition salts and metal salt complexes have a very good endoparasiticidal, in particular anthelmintic, activity and can preferably be employed in the field of veterinary medicine. Surprisingly, the substances according to the invention show a markedly better activity for combating verminoses than previously known compounds which have a similar constitution and the same direction of action.

Optionally substituted alkyl on its own or as a component of a radical in the general formulae denotes straight-chain or branched alkyl having preferably 1 to 9, in particular 1 to 5, carbon atoms. The following may be mentioned by way of example and as being preferred: optionally substituted methyl, ethyl, n- and i-propyl and n-, i- and t-butyl.

Optionally substituted alkenyl on its own or as a component of a radical in the general formulae denotes straight-chain or branched alkenyl having preferably 2 to 20, in particular 2 to 18, carbon atoms. The following may be mentioned by way of example and as being preferred: optionally substituted ethenyl, prop-1-enyl, prop-2-enyl and but-3-enyl.

Optionally substituted cycloalkyl in the general formulae denotes mono-, bi- and tricyclic cycloalkyl having preferably 3 to 10, in particular 3, 5 or 6 carbon atoms. The following may be mentioned by way of example and as being preferred: optionally substituted cyclopropyl, cyclobutyl, cyclopentyl, cyclohexyl, cycloheptyl, bicyclo[2.2.1]heptyl, bicyclo[2.2.2]octyl and adamantyl.

Optionally substituted alkoxy in the general formulae denotes straight-chain or branched alkoxy having preferably 1 to 6, in particular 1 to 4, carbon atoms. The following may be mentioned by way of example and as being preferred: optionally substituted methoxy, ethoxy, n- and i-propoxy and n-, o- and t-butoxy.

Optionally substituted alkylthio in the general formulae denotes straight-chain or branched alkylthio having preferably 1 to 6, in particular 1 to 4, carbon atoms. The following my be mentioned by way of example and as being preferred: optionally substituted methylthio, ethylthio, n- and i-propylthio and n-, o- and t-butylthio.

Halogenoalkyl in the general formulae contains 1 to 4, in particular 1 or 2, carbon atoms and preferably 1 to 9, in particular 1 to 5, identical or different halogen atoms, the halogen atoms preferably being fluorine, chlorine and bromine, in particular fluorine and chlorine. Examples which may be mentioned are trifluoromethyl, chlorodifluoromethyl, bromomethyl, 2,2,2-trifluoroethyl and pentafluoroethyl and perfluoro-t-butyl.

Optionally substituted aryl in the general formulae preferably denotes optionally substituted phenyl or naphthyl, in particular phenyl.

Optionally substituted arylalkyl in the general formulae denotes aralkyl which is optionally substituted in the aryl moiety and/or alkyl moiety, having preferably 6 or 10, in particular 8, carbon atoms in the aryl moiety (preferably phenyl or naphthyl, in particular phenyl) and preferably 1 to 4, in particular 1 or 2, carbon atoms in the alkyl moiety, it being possible for the alkyl moiety to be straight-chain or branched. The following may be mentioned by way of example and as being preferred: optionally substituted benzyl and phenylethyl.

Optionally substituted heteroaryl alone or as a component of a radical denotes in the general formulae 5- to 7-membered rings having preferably 1 to 3, in particular 1 or 2, identical or different hetero atoms. Hereto atoms are oxygen, sulphur or nitrogen. The following may be mentioned by way of example and as being preferred: optionally substituted furyl, thienyl, pyrazolyl, imidazolyl, 1,2,3- and 1,2,4-triazolyl, oxazolyl, isoxazolyl, thiazolyl, isothiazolyl, 1,2,3-, 1,3,4-, 1,2,4- and 1,2,5-oxadiazolyl, azepinyl, pyrrolyl, isopyrrolyl, pyridyl, piperazinyl, pyridazinyl, pyrimidinyl, pyrazinyl, 1,3,5-, 1,2,4- and 1,2,3-triazinyl, 1,2,4-, 1,3,2-, 1,3,6- and 1,2,6-oxazinyl, oxepinyl, thiepinyl and 1,2,4-diazepinyl.

The optionally substituted radicals of the general formulae can have one or more, preferably 1 to 3, in particular 1 to 2, identical or different substituents. The following substituents may be mentioned by way of example and as being preferred:

alkyl having preferably 1 to 4, in particular 1 or 2, carbon atoms, such as methyl, ethyl, n- and i-propyl and n-, i- and t-butyl; alkoxy having preferably 1 to 4, in particular 1 or 2, carbon atoms, such as methoxy, ethoxy, n- and i-propyloxy and n-, i- and t-butyloxy; alkylthio having preferably 1 to 4, in particular 1 or 2, carbon atoms, such as methylthio, ethylthio, n- and i-propylthio and n-, i- and t-butyltio; halogenoalkyl having preferably 1 to 4, in particular 1 or 2, carbon atoms and preferably 1 to 5, in particular 1 to 3, halogen atoms, the halogen atoms being identical or different and as halogen atoms, preferably fluorine, chlorine or bromine, in particular fluorine, such as difluoromethyl or trifluoromethyl; hydroxyl; halogen, preferably fluorine, chlorine, bromine and iodine, in particular fluorine, chlorine and bromine; cyano; nitro; amino; monoalkyl- and dialkylamino having preferably 1 to 4, in particular 1 or 2, carbon atoms per alkyl group, such as methylamino, methyl-ethyl-amino, n-and i-propylamino and methyl-n-butylamino; acyl radicals, such as carboxyl; carbalkoxy having preferably 2 to 4, in particular 2 or 3, carbon atoms, such as carbomethoxy and carboethoxy; alkylsulphinyl having 1 to 4, in particular 1 to 2, carbon atoms, halogenoalkylsulphinyl having 1 to 4, in particular 1 to 2, carbon atoms and 1 to 5 halogen atoms, such as trifluoromethylsulphinyl; sulphonyl (—SO$_3$H); alkylsulphonyl having preferably 1 to 4, in particular 1 or 2, carbon atoms, such as methylsulphonyl and ethylsulphonyl; halogenoalkylsulphonyl having 1 to 4, in particular 1 to 2, carbon atoms and 1 to 5 halogen atoms, such as trifluoromethylsulphonyl or perfluoro-t,n,s-butylsulphonyl; arylsulphonyl having preferably 6 or 10 aryl carbon atoms, such as phenylsulphonyl; acyl, aryl, aryloxy, heteroaryl, heteroaryloxy, each of which can have one of the abovementioned substituents, and the forminino radical

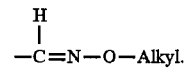

Preferred compounds of the formula (I) are those in which $R^1$ and $R^4$ independently of one another for hydrogen, straight-chain or branched $C_1$–$C_8$-alkyl, in particular methyl, ethyl, propyl, isopropyl, butyl, isobutyl, sec-butyl, tert-butyl, pentyl, isopentyl, sec-pentyl, hexyl, isohexyl, sec-hexyl, heptyl, isoheptyl sec-heptyl, tert-heptyl, octyl, isooctyl, sec-octyl, 1–5 halogen-$C_{1-4}$-alkyl, in particular trichloromethyl, trifluoromethyl, pentafluoroethyl, chlorofluoroethyl, hydroxy-$C_1$–$C_6$-alkyl, in particular hydroxymethyl, 1-hydroxyethyl, $C_1$–$C_4$-alkanoyloxy-$C_{1-C6}$-alkyl, in particular acetoxymethyl, 1-acetoxyethyl, $C_1$–$C_4$-alkoxy-$C_1$–$C_6$-alkyl, in particular methoxymethyl, 1-methoxyethyl, aryl-$C_1$–$C_4$-alkyloxy-$C_1$–$C_6$-alkyl, in particular benzyloxymethyl, 1-benzyloxyethyl, mercapto-$C_1$–$C_6$-alkyl, in particular mercaptomethyl, $C_1$–$C_4$-alkylthio- $C_1$–$C_6$-alkyl, in particular methylthioethyl, $C_1$–$C_4$-alkylsulphinyl-$C_1$–$C_6$-alkyl, in particular methylsulphinylethyl, $C_1$–$C_4$-alkylsulphonyl-$C_1$–$C_6$-alkyl, in particular methylsulphonylethyl, carboxy-$C_1$–$C_6$-alkyl, in particular carboxymethyl, carboxyethyl, $C_1$–$C_4$-alkoxycarbonyl-$C_1$–$C_6$-alkyl, in particular methoxycarbonylmethyl, ethoxycarbonylethyl, $C_1$–$C_4$-arylalkoxycarbonyl-$C_1$–$C_6$-alkyl, in particular benzyloxycarbonylmethyl, carbamoyl-$C_1$–$C_6$-alkyl, in particular carbamoylmethyl, carbamoylethyl, amino-$C_1$–$C_6$-alkyl, in particular aminopropyl, aminobutyl, $C_1$–$C_4$-alkylamino-$C_1$–$C_6$-alkyl, in particular methylaminopropyl, methylaminobutyl, $C_1$–$C_4$-dialkylamino $C_1$–$C_6$-alkyl, in particular dimethylaminopropyl, dimethylaminobutyl, guanido-$C_1$–$C_6$-alkyl, in particular guanidopropyl, $C_1$–$C_4$-alkoxycarbonylamino-$C_1$–$C_6$-alkyl, in particular tert-butoxycarbonylaminopropyl, tert-butoxycarbonylaminobutyl, 9-fluorenylmethoxycarbonyl(Fmoc)amino-$C_1$–$C_6$-alkyl, in particular 9-fluorenyl-methoxycarbonyl(Fmoc)aminopropyl, 9-fluorenylmethoxycarbonyl(Fmoc)aminobutyl, $C_3$–$C_7$-cycloalkyl, in particular cyclopentyl, cyclohexyl, cycloheptyl, $C_3$–$C_7$-cycloalkyl-$C_1$–$C_4$-alkyl, in particular cyclopentylmethyl, cyclohexylmethyl, cycloheptylmethyl, phenyl, phenyl-$C_1$–$C_4$-alkyl, in particular phenylmethyl, each of which can optionally be substituted by radicals from the series comprising halogen, in particular fluorine, chlorine bromine or iodine, hydroxyl, nitro, CN, $C_1$–$C_4$-alkoxy, in particular methoxy or ethoxy, $C_1$–$C_4$-alkyl, in particular methyl, $R^2$, $R^3$, $R^5$ and $R^6$ independently of one another for hydrogen, straight-chain or branched $C_1$–$C_8$-alkyl, in particular methyl, ethyl, propyl, isopropyl, butyl, isobutyl, sec-butyl, tert-butyl, pentyl, isopentyl, sec-pentyl, hexyl, isohexyl, sec-hexyl, heptyl, isoheptyl, sec-heptyl, tert-heptyl, octyl, isooctyl, sec-octyl, 1–5 halogen-$C_{1-4}$-alkyl, in particular trichloromethyl, trifluoromethyl, pentafluoroethyl, chlorofluoroethyl, hydroxy-$C_1$–$C_6$-alkyl, in particular hydroxymethyl, 1-hydroxyethyl, $C_1$–$C_4$-alkanoyloxy-$C_1$–$C_6$-alkyl, in particular acetoxymethyl, 1-acetoxyethyl, $C_1$–$C_4$-alkoxy-$C_1$–$C_6$-alkyl, in particular methoxymethyl, 1-methoxyethyl, aryl-$C_1$–$C_4$-alkyloxy-$C_1$–$C_6$-alkyl, in particular benzyloxymethyl, 1-benzyloxy-ethyl, mercapto-$C_1$–$C_6$-alkyl, in particular mercaptomethyl, $C_1$–$C_4$-alkylthio-$C_1$–$C_6$-alkyl, in particular methylthioethyl, $C_1$–$C_4$-alkylsulphinyl-$C_1$–$C_6$-alkyl, in particular methylsulphinylethyl, $C_1$–$C_4$-alkylsulphonyl-$C_1$–$C_6$-alkyl, in particular methylsulphonylethyl, carboxy-$C_1$–$C_6$-alkyl, in particular carboxymethyl, carboxyethyl, $C_1$–$C_4$-alkoxycarbonyl-$C_1$–$C_6$-alkyl, in particular methoxycarbonylmethyl, ethoxycarbonylethyl, $C_1$–$C_4$-arylalkoxycarbonyl-$C_1$–$C_6$-alkyl, in particular benzyloxycarbonylmethyl, carbamoyl-$C_1$–$C_6$-alkyl, in particular carbamoylmethyl, carbamoylethyl, amino-$C_1$–$C_6$-alkyl, in particular aminopropyl, aminobutyl, $C_1$–$C_4$-alkylamino-$C_1$–$C_6$-alkyl, in particular methylaminopropyl, methylaminobutyl, $C_1$–$C_4$-dialkylamino-$C_1$–$C_6$-alkyl, in particular dimethylaminopropyl, dimethylaminobutyl, $C_2$–$C_8$-alkenyl, in particular vinyl, allyl, butenyl, $C_3$–$C_7$-cycloalkyl, in particular cyclopentyl, cyclohexyl, cycloheptyl, $C_3$–$C_7$-cycloalkyl-$C_1$–$C_4$-alkyl, in particular cyclopentylmethyl, cyclohexylmethyl, cycloheptylmethyl, phenyl, phenyl-$C_1$–$C_4$-alkyl, in particular phenylmethyl, thienylmethyl, thiazolylmethyl, pyridylmethyl, each of which can optionally be substituted by radicals from the series comprising halogen, in particular fluorine, chlorine, bromine or iodine, hydroxyl, sulphonyl ($SO_3H$), CN, $NO_2$, amino, di($C_1$–$C_4$-alkyl) amino, for example dimethylamino, $C_1$–$C_4$-alkoxy, in particular methoxy or ethoxy, $C_1$–$C_4$-alkyl, in particular methyl, and their optical isomers and racemates Particularly preferred compounds of the formula (I) are those in which $R^1$ and $R^4$ independently of one another for hydrogen, straight-chain or branched $C_1$–$C_8$-alkyl, in particular methyl, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl, sec-octyl, 1–5 halogen-$C_{1-4}$-alkyl, in particular trichloromethyl, trifluoromethyl, pentafluoroethyl, chlorofluoroethyl, hydroxy-$C_1$–$C_6$-alkyl, in particular hydroxymethyl, 1-hydroxyethyl, $C_1$–$C_4$-alkanoyloxy-$C_1$–$C_6$-alkyl, in particular acetoxymethyl, 1-acetoxyethyl, $C_1$–$C_4$-alkoxy-$C_1$–$C_6$-alkyl, in particular methoxymethyl, 1-methoxyethyl, aryl -$C_1$–$C_4$-alkyloxy-$C_1$–$C_6$-alkyl, in particular benzyloxymethyl, 1-benzyloxyethyl, $C_1$–$C_4$-alkoxycarbonylamino-$C_1$–$C_6$-alkyl, in particular tert-butoxycarbonylaminopropyl, tert-butoxycarbonylaminobutyl, $C_3$–$C_7$-cycloalkyl, in particular cyclopentyl, cyclohexyl, cycloheptyl, $C_3$–$C_7$-cycloalkyl-$C_1$–$C_4$-alkyl, in particular cyclopentylmethyl, cyclohexylmethyl, cycloheptylmethyl, phenyl-$C_1$–$C_4$-alkyl, in particular phenylmethyl, each of which can optionally be substituted by one or more identical or different radicals from among those mentioned above, $R^2$, $R^3$, $R^5$ and $R^6$ independently of one another for hydrogen, straight-chain or branched $C_1$–$C_8$-alkyl, in particular methyl, ethyl, propyl, isopropyl, butyl, isobutyl, sec-butyl, tert-butyl, pentyl, isopentyl, sec-pentyl, hexyl, isohexyl, sec-hexyl, heptyl, isoheptyl, sec-heptyl, tert-heptyl, octyl, isooctyl, sec-octyl, 1–5 halogen-$C_{1-4}$-alkyl, in particular trichloromethyl, trifluoromethyl, pentafluoroethyl, chlorofluoroethyl, hydroxy-$C_1$–$C_6$-alkyl, in particular hydroxymethyl, aryl-$C_1$–$C_4$-alkyloxy-$C_1$–$C_6$-alkyl, in particular benzyloxymethyl, 1-benzyloxyethyl, carboxy-$C_1$–$C_6$-alkyl, in particular carboxymethyl, carboxyethyl, $C_1$–$C_4$-alkoxycarbonyl-$C_1$–$C_6$-alkyl, in particular methoxycarbonylmethyl, ethoxycarbonylethyl, $C_1$–$C_4$-aryl-alkoxycarbonyl-$C_1$–$C_6$-alkyl, in particular benzyloxycarbonylmethyl, $C_1$–$C_4$-alkylamino-$C_1$–$C_6$-alkyl, in particular methylaminopropyl, methylaminobutyl, $C_1$–$C_6$-dialkylamino-$C_1$–$C_6$-alkyl, in particular dimethylaminopropyl, dimethylaminobutyl, $C_2$–$C_8$-alkenyl, in particular vinyl, allyl, butenyl, $C_3$–$C_7$-cycloalkyl, in particular cyclopentyl, cyclohexyl, cycloheptyl, $C_3$–$C_7$-cycloalkyl-$C_1$–$C_4$-alkyl, in particular cyclopentylmethyl, cyclohexylmethyl, cycloheptylmethyl, phenyl, phenyl-$C_1$–$C_4$-alkyl, in particular phenylmethyl, thienylmethyl, each of which can optionally be substituted by one or more identical or different radicals from among those mentioned above, and their optical isomers and racemates.

Very particularly preferred compounds of the formula (I) are those
in which

R$^1$ and R$^4$ independently of one another represent hydrogen, straight-chain or branched C$_1$-C$_8$-alkyl, in particular methyl, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl, sec-octyl, C$_3$-C$_7$-cycloalkyl-C$_1$-C$_4$-alkyl, in particular cyclohexylmethyl, phenyl-C$_1$-C$_4$-alkyl, in particular phenylmethyl, R$^2$, R$^3$, R$^5$ and R$^6$ independently of one another for hydrogen, straight-chain or branched C$_1$-C$_8$-alkyl, in particular methyl, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl, sec-octyl, 1–5 halogen-C$_{1-4}$-alkyl, in particular trichloromethyl, trifluoromethyl, pentafluoroethyl, chlorofluoroethyl, C$_2$-C$_8$-alkenyl, in particular vinyl, allyl, C$_3$-C$_7$-cycloalkyl-C$_1$-C$_4$-alkyl, in particular cyclohexylmethyl, phenyl-C$_1$-C$_4$-alkyl, in particular phenylmethyl, thienylmethyl, each of which can optionally be substituted by one or more identical or different radicals from among those mentioned above, and their optical isomers and racemates.

The compounds of the general formula (I) can exist and can be used in optically active, stereoisomeric forms or in the form of racemic mixtures. The optically active, stereoisomeric forms of the compounds of the general formula (I) are preferably used.

The following compounds of the general formula (I) in which the radicals R$^1$ to R$^6$ have the meaning given below may be mentioned individually:

| R$^1$ | R$^2$ | R$^3$ | R$^4$ | R$^5$ | R$^6$ |
|---|---|---|---|---|---|
| —CHMeCH$_2$Me | —Cyclohexyl | —CHMeCH$_2$Me | —Me | —CHMeCH$_2$Me | —Me |
| —CHMeCH$_2$Me | —Cyclohexyl | —CHMeCH$_2$Me | —Me | —CHMeCH$_2$Me | —Cyclohexyl |
| —CHMeCH$_2$Me | —CH$_2$—Phe | —CHMeCH$_2$Me | —Me | —CHMeCH$_2$Me | —Me |
| —CHMeCH$_2$Me | —CH$_2$—Phe | —CHMeCH$_2$Me | —Me | —CHMeCH$_2$Me | —CH$_2$—Phe |
| —CHMeCH$_2$Me | —(CH$_2$)$_3$—Me | —CHMeCH$_2$Me | —Me | —CHMeCH$_2$Me | —Me |
| —CHMeCH$_2$Me | —(CH$_2$)$_3$—Me | —CHMeCH$_2$Me | —Me | —CHMeCH$_2$Me | —(CH$_2$)$_3$—Me |
| —CHMe$_2$ | —CH$_2$—Phe | —CHMeCH$_2$Me | —Me | —CHMeCH$_2$Me | —Me |
| —CH$_2$—Phe | —CHMe$_2$ | —CH$_2$—Phe | —CHMe$_2$ | —CHMeCH$_2$Me | —CHMe$_2$ |
| —CH$_2$CHMe$_2$ | —CH$_2$—Phe | —CH$_2$CHMe$_2$ | —Me | —CH$_2$CHMe$_2$ | —CH$_2$—Phe |
| —(CH$_2$)$_3$—Me | —Me | —CHMeCH$_2$Me | —Me | —CHMeCH$_2$Me | —Me |
| —CHMe$_2$ | —Me | —CHMe$_2$ | —Me | —CHMe$_2$ | —Me |
| —CH$_2$—Me | —Me | —CH$_2$—Me | —Me | —CH$_2$—Me | —Me |
| —(CH$_2$)$_2$—Me | —Me | —(CH$_2$)$_2$ | —Me | —(CH$_2$)$_2$—Me | —Me |
| —(CH$_2$)$_3$—Me | —Me | —(CH$_2$)$_3$—Me | —Me | —(CH$_2$)$_3$—Me | —Me |
| —CH$_2$—CH=CH$_2$ | —Me | —CH$_2$—CH=CH$_2$ | —Me | —(CH$_2$)—CH=CH$_2$ | —Me |
| —CHMeCH$_2$Me | —Me | —CHMeCH$_2$Me | —Me | —CHMeCH$_2$Me | —CH$_2$—Me |
| —CHMeCH$_2$Me | —Me | —CHMeCH$_2$Me | —Me | —CHMeCH$_2$Me | —(CH$_2$)$_2$—Me |
| —CHMeCH$_2$Me | —Me | —CHMeCH$_2$Me | —Me | —CHMeCH$_2$Me | —(CH$_2$)$_3$—Me |
| —CHMeCH$_2$Me | —Me | —CHMeCH$_2$Me | —Me | —CH$_2$Me | —Me |
| —CHMeCH$_2$Me | —Me | —CHMeCH$_2$Me | —Me | —(CH$_2$)$_2$—Me | —Me |
| —Cyclohexyl | —Me | —Cyclohexyl | —Me | —Cyclohexyl | —Me |
| —CH$_2$CHMe$_2$ | —Cyclohexyl | —CH$_2$CHMe$_2$ | —Me | —CH$_2$CHMe$_2$ | —Cyclohexyl |
| —CH$_2$CHMe$_2$ | —Cyclohexyl | —CH$_2$CHMe$_2$ | —Me | —CH$_2$CHMe$_2$ | —Me |
| —CHMeCH$_2$Me | —CHMe$_2$ | —CHMeCH$_2$Me | —CHMe$_2$ | —CHMeCH$_2$Me | —Me |
| —CH$_2$—Phe | —Me | —CH$_2$—Phe | —Me | —CH$_2$—Phe | —Me |
| —Cyclohexyl | —Me | —Cyclohexyl | —Me | —Cyclohexyl | —Me |
| —CHMe$_2$ | —CHMe$_2$ | —CHMe$_2$ | —Me | —CHMe$_2$ | —Me |
| —CHMe$_2$ | —CHMe$_2$ | —CHMe$_2$ | —CHMe$_2$ | —CHMe$_2$ | —Me |
| —CH$_2$—Me | —CHMe$_2$ | —CH$_2$Me | —Me | —CH$_2$—Me | —Me |
| —CH$_2$—Me | —CHMe$_2$ | —CH$_2$Me | —CHMe$_2$ | —CH$_2$—Me | —Me |
| —(CH$_2$)$_2$—Me | —CHMe$_2$ | —(CH$_2$)$_2$—Me | —Me | —(CH$_2$)$_2$—Me | —Me |
| —(CH$_2$)$_2$—Me | —CHMe$_2$ | —(CH$_2$)$_2$—Me | —CHMe$_2$ | —(CH$_2$)$_2$—Me | —Me |
| —(CH$_2$)$_3$—Me | —CHMe$_2$ | —(CH$_2$)$_3$—Me | —Me | —(CH$_2$)$_3$—Me | —Me |
| —(CH$_2$)$_3$—Me | —CHMe$_2$ | —(CH$_2$)$_3$—Me | —CHMe$_2$ | —(CH$_2$)$_3$—Me | —Me |
| —CH$_2$—CH=CH$_2$ | —CHMe$_2$ | —CH$_2$—CH=CH$_2$ | —Me | —CH$_2$—CH=CH$_2$ | —Me |
| —CH$_2$—CH=CH$_2$ | —CHMe$_2$ | —CH$_2$—CH=CH$_2$ | —CHMe$_2$ | —CH$_2$—CH=CH$_2$ | —Me |
| —Me | —CH$_2$CHMe$_2$ | Me | Me | —CH$_2$CHMe$_2$ | —CH$_2$—C$_6$H$_4$—NO$_2$ |
| —Me | —CH$_2$CHMe$_2$ | Me | Me | —CH$_2$CHMe$_2$ | —CH$_2$—C$_6$H$_4$—NH$_2$ |
| —Me | —CH$_2$CHMe$_2$ | Me | Me | —CH$_2$CHMe$_2$ | —CH$_2$—C$_6$H$_4$—NMe$_2$ |

-continued

| R¹ | R² | R³ | R⁴ | R⁵ | R⁶ |
|---|---|---|---|---|---|
| —Me | —CH₂CHMe₂ | Me | Me | —CH₂CHMe₂ | —CH₂—C₆H₄—SO₃H |
| —Me | —CH₂CHMe₂ | Me | Me | —CH₂CHMe₂ | —CH₂-(2-thienyl) |

Me = methyl; Phe = phenyl;

Preferred and particularly preferred amongst the new compounds of the general formula (Ia) are those in which the substituents have the definitions given above as being preferred.

Some of the compounds of the general formula (I) are known (see above) or can be obtained by the processes mentioned there.

The new compounds of the formula (I) can be prepared by the process applied by U. Schmidt et al. to macrocyclic peptide alkaloids (cf. for example: U. Schmidt et al. in Synthesis (1991) pp. 294–300 [didemnin A, B and C]; Angew. Chem. 96 (1984) pp. 723–724 [dolastatin 3]; Angew. Chem. 102 (1990) pp. 562–563 [fenestin A]; Angew. Chem. 97 (1985) pp. 606–607 [ulicyclamid]; J. Org. Chem. 47 (1982) pp. 3261–3264).

The compounds of the general formula (I) can be prepared by the processes indicated above under item 3.

If, in process 3 for the preparation of the new cyclic depsipeptides (I), N-methyl-L-isoleucyl-D-lactyl-N-methyl-L-isoleucyl-D-lactic acid is employed as compounds of the formula (II), the process can be represented by the following equation:

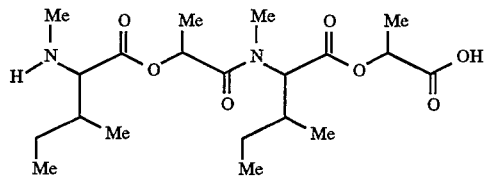

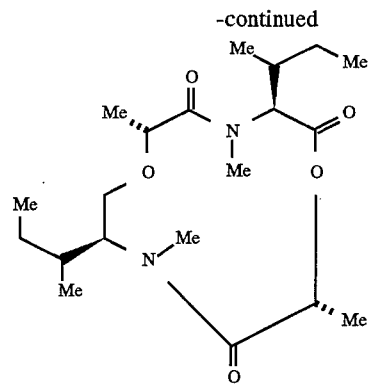

Formula (II) provides a general definition of the opening-chain tetradepsipeptides required as starting substances for carrying out process 3. In this formula, R¹ to R⁶ preferably represent those radicals which have already been mentioned in connection with the description of the substances of the formula (I) according to the invention as being preferred for these substituents.

The tetradepsipeptides of the formula (II), which are used as starting materials, are new. Their preparation is described further below.

The following compounds of the general formula (II), in which the radicals R¹ to R⁶ have the following meaning, may be mentioned individually:

| R¹ | R² | R³ | R⁴ | R⁵ | R⁶ |
|---|---|---|---|---|---|
| —CHMeCH₂Me | —Cyclohexyl | —CHMeCH₂Me | —Me | —CHMeCH₂Me | —Me |
| —CHMeCH₂Me | —Cyclohexyl | —CHMeCH₂Me | —Me | —CHMeCH₂Me | —Cyclohexyl |
| —CHMeCH₂Me | —CH₂—Phe | —CHMeCH₂Me | —Me | —CHMeCH₂Me | —Me |
| —CHMeCH₂Me | —CH₂—Phe | —CHMeCH₂Me | —Me | —CHMeCH₂Me | —CH₂—Phe |
| —CHMeCH₂Me | —(CH₂)₃—Me | —CHMeCH₂Me | —Me | —CHMeCH₂Me | —Me |
| —CHMeCH₂Me | —(CH₂)₃—Me | —CHMeCH₂Me | —Me | —CHMeCH₂Me | —Me |
| —CHMeCH₂Me | —(CH₂)₃—Me | —CHMeCH₂Me | —Me | —CHMeCH₂Me | —(CH₂)₃—Me |
| —CHMe₂ | —CH₂—Phe | —CHMeCH₂Me | —Me | —CHMeCH₂Me | —Me |
| —CH₂—Phe | —CHMe₂ | —CH₂—Phe | —CHMe₂ | —CHMeCH₂Me | —CHMe₂ |
| —CH₂CHMe₂ | —CH₂—Phe | —CH₂CHMe₂ | —Me | —CH₂CHMe₂ | —CH₂—Phe |
| —CH₂—Me | —Me | —CH₂—Me | —Me | —CH₂—Me | —Me |
| —(CH₂)₂—Me | —Me | —(CH₂)₂—Me | —Me | —(CH₂)₂—Me | —Me |
| —(CH₂)₃—Me | —Me | —(CH₂)₃—Me | —Me | —(CH₂)₃—Me | —Me |
| —CH₂—CH=CH₂ | —Me | —CH₂—CH=CH₂ | —Me | —CH₂—CH=CH₂ | —Me |
| —CHMeCH₂Me | —Me | —CHMeCH₂Me | —Me | —CHMeCH₂Me | —CH₂—Me |
| —CHMeCH₂Me | —Me | —CHMeCH₂Me | —Me | —CHMeCH₂Me | —(CH₂)₂—Me |
| —CHMeCH₂Me | —Me | —CHMeCH₂Me | —Me | —CHMeCH₂Me | —(CH₂)₃—Me |

-continued

| R¹ | R² | R³ | R⁴ | R⁵ | R⁶ |
|---|---|---|---|---|---|
| —CHMeCH₂Me | —Me | —CHMeCH₂Me | —Me | —CH₂Me | —Me |
| —CHMeCH₂Me | —Me | —CHMeCH₂Me | —Me | —(CH₂)₂—Me | —Me |
| —Cyclohexyl | —Me | —Cyclohexyl | —Me | —Cyclohexyl | —Me |
| —CH₂CHMe₂ | —Cyclohexyl | —CH₂CHMe₂ | —Me | —CH₂CHMe₂ | —Cyclohexyl |
| —CH₂CHMe₂ | —Cyclohexyl | —CH₂CHMe₂ | —Me | —CH₂CHMe₂ | —Me |
| —CHMeCH₂Me | —CHMe₂ | —CHMeCH₂Me | —CHMe₂ | —CHMeCH₂Me | —Me |
| —CH₂—Phe | —Me | —CH₂—Phe | —Me | —CH₂—Phe | —Me |
| —Cyclohexyl | —Me | —Cyclohexyl | —Me | —Cyclohexyl | —Me |
| —CHMe₂ | —CHMe₂ | —CHMe₂ | —Me | —CHMe₂ | —Me |
| —CHMe₂ | —CHMe₂ | —CHMe₂ | —CHMe₂ | —CHMe₂ | —Me |
| —CH₂—Me | —CHMe₂ | —CH₂—Me | —Me | —CH₂—Me | —Me |
| —CH₂—Me | —CHMe₂ | —CH₂—Me | —CHMe₂ | —CH₂—Me | —Me |
| —(CH₂)₂—Me | —CHMe₂ | —(CH₂)₂—Me | —Me | —(CH₂)₂—Me | —Me |
| —(CH₂)₂—Me | —CHMe₂ | —(CH₂)₂—Me | —CHMe₂ | —(CH₂)₂—Me | —Me |
| —(CH₂)₃—Me | —CHMe₂ | —(CH₂)₃—Me | —Me | —(CH₂)₃—Me | —Me |
| —(CH₂)₃—Me | —CHMe₂ | —(CH₂)₃—Me | —CHMe₂ | —(CH₂)₃—Me | —Me |
| —CH₂—CH=CH₂ | —CHMe₂ | —CH₂—CH=CH₂ | —Me | —CH₂—CH=CH₂ | —Me |
| —CH₂—CH=CH₂ | —CHMe₂ | —CH₂—CH=CH₂ | —CHMe₂ | —CH₂—CH=CH₂ | —Me |
| —Me | —CH₂CHMe₂ | Me | Me | —CH₂CHMe₂ | —CH₂—C₆H₄—NO₂ |
| —Me | —CH₂CHMe₂ | Me | Me | —CH₂CHMe₂ | —CH₂—C₆H₄—NH₂ |
| —Me | —CH₂CHMe₂ | Me | Me | —CH₂CHMe₂ | —CH₂—C₆H₄—NMe₂ |
| —Me | —CH₂CHMe₂ | Me | Me | —CH₂CHMe₂ | —CH₂—C₆H₄—SO₃H |
| —Me | —CH₂CHMe₂ | Me | Me | —CH₂CHMe₂ | —CH₂—(thienyl, S) |

Me = methyl; Phe = phenyl.

In process 3, tetradepsipeptides are subjected to a cyclization reaction in the presence of diluents and suitable coupling reagents.

Suitable coupling reagents are all those compounds, which are suitable for producing an amine linkage (cf. for example: Houben-Weyl, Methoden der Organischen Chemie [Methods in Organic Chemistry], Vol. 15/2; Bodanzky et al., Peptide Synthesis 2nd ed., Wiley and Sons, New York 1976).

The following methods are preferably suitable: active ester method using pentafluorophenol (PfP), N-hydroxysuccinimide, 1-hydroxybenzotriazole, coupling with carbodiimides, such as dicyclohexylcarbodiimide or N'-(3-dimethylaminopropyl)-N-ethylcarbodiimide (EBC), and the mixed anhydride method, or coupling with phosphonium reagents, such as benzotriazol-1-yl-oxy-tris(dimethylaminophosphonium) hexafluorophosphate (BOP), bis-(2-oxo-3-oxazolidinyl)-phosphonium acid chloride (BOP-Cl), or with phosphonic ester reagents, such as cyanophosphonium acid diethyl ester (DEPC) and diphenylphosphoryl azide (DPPA).

Particularly preferred is coupling with bis(2-oxo-3-oxazolidinyl)-phosphinic chloride (BOP-Cl) and N'-(3-dimethylaminopropyl)-N-ethylcarbodiimide (EDC) in the presence of 1-hydroxybenzotriazole (HOBt).

The reaction is carried out at temperatures from 0° to 150° C., preferably at 20° to 100° C., particularly preferably at room temperature.

Suitable diluents are all the inert organic solvents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, furthermore ethers, such as diethyl ether, dibutyl ether, glycol dimethyl ether and diglycol dimethyl ether, tetrahydrofuran and dioxane, furthermore ketones, such as acetone, methyl ethyl ketone, methyl isopropyl ketone and methyl isobutyl ketone, moreover esters, such as methyl acetate and ethyl acetate, furthermore nitriles such as, for example, acetonitrile and propionitrile, benzonitrile and glutaronitrile, in addition amides such as, for example, dimethylformamide, dimethylacetamide and N-methylpyrrolidone, and also dimethyl sulphoxide, tetramethylene sulphone and hexamethylphosphoric triamide.

The cyclization is carried out in the presence of a base.

Suitable bases are inorganic and organic bases. The following may be mentioned as bases: hydroxides, carbonates, hydrogencarbonates and alcoholates of alkali metals and alkaline earth metals, furthermore amines such as, in particular, tertiary amines, for example trimethylamine, triethylamine, N-methylmorpholine, pyridine, picolines, N-ethylpyrrolidine, diazabicyclo(4.3.0)-undecene (DBU), 1,4-diazabicyclo(2.2.2)octane (DABCO), diazahicyclo(3,2,0)nonene (DBN), ethyl-diisopropylamine.

The compounds of the formulae (II) and the bases are employed in a ratio of 1:1 to 1:1.5 to each other. An approximately equimolar ratio is preferred.

When the reaction has ended, the diluent is distilled off, and the compounds of the formula (I) purified in the customary manner, for example by chromatography.

These reaction conditions also apply when carrying out processes 11, 17 and 19.

The tetradepsipeptides of the formula (II) which are used as starting compounds can be prepared by processes known per se, for example as is described by H.-G. Lerchen and H. Kunz (Tetrahedron Lett. 26 (43) (1985) pp. 5257–5260; 28 (17) (1987) pp. 1873–1876) using the esterification method as described by B. F. Gisin (Helv. Chim. Acta 56 (1973) p. 1476).

Some of the amino acids and 2-halogenocarboxylic acid derivatives which are used as starting substances are known (cf. for example: N-methyl-amino acids: R. Bowmann et al. J. Chem. Soc. (1950) p. 1346; J. R. McDermott et al. Can. J. Chem. 51 (1973) p. 1915; H. Wurziger et al., Kontakte [Catalysts] (Merck. Darmstadt) 3 (1987) p. 8; 2-halogenocarboxylic acid derivatives: S. M. Birnbaum et al. J. Amer. Chem. Soc. 76 (1954) p. 6054, C. S. Rondestvedt, Jr. et al. Org. Reactions 11 (1960) p. 189 [Review]) or can be obtained by the processes described in these publications.

The coupling reagents mentioned in process 3 are used for the coupling reaction for the synthesis of the depsipeptides of the formulae (II), (V), (VIII=and (IX), which are employed as starting compounds.

The open-chain tetradepsipeptides of the formula (II) can be obtained by a process which embraces the following series of steps:

a) Synthesis of the didepsipeptides of the formulae (VIII) and (IX) by processes 17 and 19:

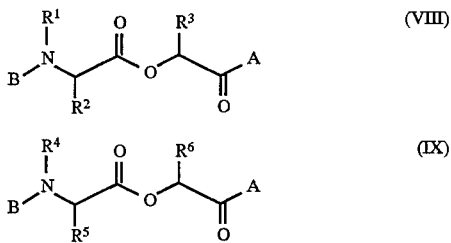

in which B denotes an N-terminal protective group, such as, for example, the benzyl or benzyloxycarbonyl group, and A denotes a C-terminal protective group, such as, for example, the tert-butoxy group.

In the case of formula (VIII), for example this follows the equation below:

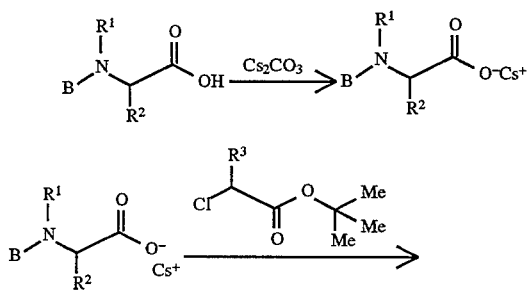

-continued

If appropriate, the enantiomerically pure compounds of the formulae (VIII) and (IX) according to the invention can optionally also be prepared by separation of the diastereomers by customary methods, such as, for example, crystallization, by column chromatography or by countercurrent distribution. A decision about the optimum process will have to be made in every individual case; sometimes it is also expedient to use combinations of the individual processes.

At the end of this step, the N-terminal protective group can be eliminated from the compounds of the formula (IX) in a manner known per se, for example by catalytic hydrogenation, to prepare the derivatives of the formula (VII). The C-terminal protective group can be eliminated from the derivatives of the formula (VIII) in a manner known per se to synthesize the compounds of the formula (VI).

The tetradepsipeptides of the formula (V) are synthesized from the didepsipeptides of the formulae (VI) and (VII) by the following equation (process 11):

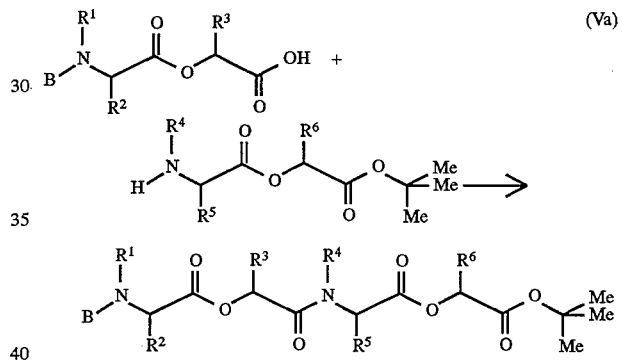

The N-terminal protective group can subsequently be removed from the compounds of the formula (Va), for example by catalytic hydrogenation as indicated above, to prepare the compounds of the formula (III), or by removing the C-terminal protective group from the compounds of the formula (V) by means of hydrolysis to give compounds of the formula (IV).

The elimination of the N-terminal protective groups by hydrogenolysis in processes 5b), 7 and 15 is particularly preferably carried out using hydrogenating agents, such as hydrogen in the presence of the customary hydrogenation catalysts, such as, for example, Raney nickel, palladium and platinum.

The process is preferably carried out using diluents. Suitable diluents are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, methyl tert-butyl ether, glycol dimethyl ether and diglycol dimethyl ether, tetrahydrofuran and dioxane, esters, such as methyl acetate and ethyl acetate, nitriles, such as, for example, acetonitrile and propionitrile, amides, such as, for example, dimethylformamide, dimethylacetamide and N-methylpyrrolidone, and also dimethyl sulphoxide, tetramethylene sulphone and hexamethylphosphoric triamide; furthermore also alcohols, such as methanol, ethanol, propanol, isopropanol, butanol, isobutanol, sec-butanol, tert-butanol, pentanol, isopentanol, sec-pentanol and tert-pentanol, and also water.

When carrying out the process according to the invention, the reaction temperatures can be varied within a substantial range. In general, the process is carried out at temperatures between −20° C. and +200° C., preferably at temperatures between 0° C. and 120° C.

The process is generally carried out under atmospheric pressure. However, it is also possible to carry out the process under elevated pressure, in general between 10 and 100 bar.

The elimination of the C-terminal protective groups by hydrolysis in processes 5a), 9 and 13 is preferably carried out using diluents.

Diluents which are suitable are virtually all inert organic solvents. These preferably include aliphatic and aromatic, optionally halogenated hydrocarbons, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methylpyrrolidone, and also dimethyl sulphoxide, tetramethylene sulphone and hexamethylphosphoric triamide.

The reaction is carried out in the presence of inorganic or organic protonic acids. Examples of such protonic acids which may be mentioned are: hydrochloric acid, sulphuric acid, trifluoroacetic acid, acetic acid and formic acid.

The reaction is carried out at temperatures between −20° and +50° C., preferably between −10° and +20° C., under atmospheric pressure or elevated pressure. It is preferably carried out under atmospheric pressure.

While having low toxicity to warm-blooded species, the active compounds are suitable for combating pathogenic endoparasites which occur in humans and in animal keeping and livestock breeding in productive livestock, breeding animals, zoo animals, laboratory animals, experimental animals and pets. In this context, they are active against all or individual stages of development of the pests and against resistant and normally sensitive species. By combating the pathogenic endoparasites, it is intended to reduce disease, deaths and decreasing performance (for example in the production of meat, milk, wool, hides, eggs, honey etc.), so that more economical and simpler animal keeping is possible by using the active compounds. The pathogenic endoparasites include Cestodes, Trematodes, Nematodes and Acantocephala, in particular:

From the order of the Pseudophyllidea, for example: Diphyllobothrium spp., Spirometra spp., Schistocephalus spp., Ligula spp., Bothridium spp., Diphlogonoporus spp.

From the order of the Cyclophyllidea, for example: Mesocestoides spp., Anoplocephala spp., Paranoplocephala spp., Moniezia spp., Thysanosomsa spp., Thysaniezia spp., Avitellina spp., Stilesia spp., Cittotaenia spp., Andyra spp., Bertiella spp., Taenia spp., Echinococcus spp., Hydatigera spp., Davainea spp., Raillietina spp., Hymenolepis spp., Echinolepis spp., Echinocotyle spp., Diorchis spp., Dipylidium spp., Joyeuxiella spp., Diplopylidium spp.

From the subclass of the Monogenea, for example: Gyrodactylus spp., Dactylogyrus spp., Polystoma spp.

From the subclass of the Digenea, for example: Diplostomum spp., Posthodiplostomum spp., Schistosoma spp., Trichobilharzia spp., Ornithobilharzia spp., Austrobilharzia spp., Gigantobilharzia spp., Leucochloridium spp., Brachylaima spp., Echinostoma spp., Echinoparyphium spp., Echinochasmus spp., Hypoderaeum spp., Fasciola spp., Fasciolides spp., Fasciolopsis spp., Cyclocoelum spp., Typhlocoelum spp., Paramphistomum spp., Calicophoron spp., Cotylophoron spp., Gigantocotyle spp., Fischoederius spp., Gastrothylacus spp., Notocotylus spp., Catatropis spp., Plagiorchis spp., Prosthogonimus spp., Dicrocoelium spp., Eurytrema spp., Troglotrema spp., Paragonimus spp., Collyriclum spp., Nanophyetus spp., Opisthorchis spp., Clonorchis spp., Metorchis spp., Heterophyes spp., Metagonismus spp.

From the order of the Enoplida, for example: Trichuris spp., Capillaria spp., Trichomosoides spp., Trichinella spp.

From the order of the Rhabditia, for example: Micronema spp., Strongyloides spp.

From the order of the Strongylida, for example: Stronylus spp., Triodontophorus spp., Oesophagodontus spp., Trichonema spp., Gyalocephalus spp., Cylindropharynx spp., Poteriostomum spp., Cyclococercus spp., Cylicostephanus spp., Oesophagostomum spp., Chabertia spp., Stephanurus spp., Ancylostoma spp., Uncinaria spp., Bunostomum spp., Globocephalus spp., Syngamus spp., Cyathostoma spp., Metastrongylus spp., Dictyocaulus spp., Muellerius spp., Protostrongylus spp., Neostrongylus spp., Cystocaulus spp., Pneumostrongylus spp., Spicocaulus spp., Elaphostrongylus spp., Parelaphostrongylus spp., Crenosoma spp., Paracrenosoma spp., Angiostrongylus spp., Aelurostrongylus spp., Filaroides spp., Parafilaroides spp., Trichostrongylus spp., Haemonchus spp., Ostertagia spp., Marshallagia spp., Cooperia spp., Nematodirus spp., Hyostrongylus spp., Obeliscoides spp., Amidostomum spp., Ollulanus spp.

From the order of the Oxyurida, for example: Oxyuris spp., Enterobius spp., Passalurus spp., Syphacia spp., Aspiculuris spp., Heterakis spp.

From the order of the Ascaridia, for example: Ascaris spp., Toxascaris spp., Toxocara spp., Parascaris spp., Anisakis spp., Ascaridia spp.

From the order of the Spirurida, for example: Gnathostoma spp., Physaloptera spp., Thelazia spp., Gongylonema spp., Habronema spp., Parabronema spp., Draschia spp., Dracunculus spp.

From the order of the Filariida, for example: Stephanofilaria spp., Parafilaria spp., Setaria spp., Loa spp., Dirofilaria spp., Litomosoides spp., Brugia spp., Wuchereria spp., Onchocerca spp.

From the order of the Gigantorhynchida, for example: Filicollis spp., Moniliformis spp., Macracanthorhynchus spp., Prosthenorchis spp.

The productive livestock and breeding animals include mammals such as, for example, cattle, horses, sheep, pigs, goats, camels, water buffalo, donkeys, rabbits, fallow deer, reindeer, fur-bearing animals such as, for example, mink, chinchilla, racoon, birds such as, for example, chickens, geese, turkeys, ducks, freshwater and salt-water fish such as, for example, trout, carps, eels, reptiles, insects such as, for example, honeybee and silkworm.

Laboratory animals and experimental animals include mice, rats, guinea pigs, golden hamsters, dogs and cats.

Pets include dogs and cats.

Administration can be effected prophylactically as well as therapeutically.

The active compounds, directly or in the form of suitable preparations, are administered enterally, parenterally, dermally, nasally, by environment treatment, or with the aid of active-compound-containing shaped articles such as, for example, strips, plates, bands, collars, ear marks, limb bands, marking devices.

The active compounds are administered enterally, for example orally, in the form of powder, tablets, capsules, pastes, drinks, granules, or solutions, suspensions and emulsions which can be administered orally, or boli, medicated feed or drinking water. Dermal administration is effected, for example, in the form of dipping, spraying or pouring-on and spotting-on. Parenteral administration is effected, for example, in the form of injection (intramuscularly, subcutaneously, intravenously, intraperitoneally) or by implants.

Suitable preparations are:

Solutions such as injectable solutions, oral solutions, concentrates for oral administration after dilution, solutions for use on the skin or in body cavities, pour-on and spot-on formulations, gels;

Emulsions and suspensions for oral or dermal administration and for injection; semi-solid preparations;

Formulations in which the active compound is incorporated in a cream base or in an oil-in-water or water-in-oil emulsion base;

Solid preparations such as powders, premixes or concentrates, granules, pellets, tablets, boli, capsules; aerosols and inhalants, shaped articles containing active compound.

Injectable solutions are administered intravenously, intramuscularly and subcutaneously.

Injectable solutions are prepared by dissolving the active compound in a suitable solvent and, if appropriate, adding additives such as solubilizers, acids, bases, buffer salts, antioxidants and preservatives. The solutions are sterile-filtered and drawn off.

The following may be mentioned as solvents: Physiologically acceptable solvents such as water, alcohols such as ethanol, butanol, benzyl alcohol, glycerol, propylene glycol, polyethylene glycols, N-methyl-pyrrolidone, and mixtures of these.

If appropriate, the active compounds can also be dissolved in physiologically acceptable vegetable or synthetic oils which are suitable for injection.

The following may be mentioned as solubilizers: solvents which enhance solution of the active compound in the main solvent, or which prevent its precipitation. Examples are polyvinylpyrrolidone, polyoxyethylated castor oil, polyoxyethylated sorbitan esters.

Preservatives are: benzyl alcohol, trichlorobutanol, p-hydroxybenzoic esters, n-butanol.

Oral solutions are administered directly. Concentrates are administered orally after previously having been diluted to the administration concentration. Oral solutions and concentrates are prepared as described above in the case of the injectable solutions, it being possible to dispense with working under sterile conditions.

Solutions for use on the skin are applied dropwise, brushed on, rubbed in, splashed on or sprayed on. These solutions are prepared as described above in the case of injectable solutions.

It may be advantageous to add thickeners during the preparation. Thickeners are: inorganic thickeners such as bentonite, colloidal silica, aluminium monostearate, organic thickeners such as cellulose derivatives, polyvinyl alcohols and their copolymers, acrylates and methacrylates.

Gels are applied to, or brushed on, the skin, or introduced into body cavities. Gels are prepared by treating solutions which have been prepared as described in the case of the injectable solutions with such an amount of thickener that a clear substance of cream-like consistency is formed. Thickeners employed are the thickeners indicated further above.

Pour-on and spot-on formulations are poured onto, or splashed onto, limited areas of the skin, the active compound penetrating the skin and acting systemically.

Pour-on and spot-on formulations are prepared by dissolving, suspending or emulsifying the active compound in suitable solvents or solvent mixtures which are tolerated by the skin. If appropriate, other adjuvants such as colourants, absorption accelerators, antioxidants, light stabilizers, and tackifiers are added.

Solvents which may be mentioned are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, aromatic and/or aliphatic hydrocarbons, vegetable or synthetic oils, DMF, dimethylacetamide, N-methyl-pyrrolidone, 2,2-dimethyl-4-oxy-methylene-1,3-dioxolane.

Colourants are all colourants which are licensed for use on animals and which can be dissolved or suspended.

Examples of absorption accelerators are DMSO, spreading oils such as isopropyl myristate, dipropylene glycol pelargonate, silicone oils, fatty acid esters, triglycerides, fatty alcohols.

Antioxidants are sulphites or metabisulphites such as potassium metabisulphite, ascorbic acid, butylhydroxytoluene, butylhydroxyanisole, tocopherol.

Examples of light stabilizers are novantisolic acid.

Examples of tackifiers are cellulose derivatives, starch derivatives, polyacrylates, natural polymers such as alginates, gelatine.

Emulsions can be administered orally, dermally or in the form of injections.

Emulsions are either of the water-in-oil type or of the oil-in-water type.

They are prepared by dissolving the active compound either in the hydrophobic or in the hydrophilic phase and homogenising this phase with the solvent of the other phase, with the aid of suitable emulsifiers and, if appropriate, other adjuvants such as colourants, resorption accelerators, preservatives, antioxidants, light stabilizers, viscosity-increasing substances.

The following may be mentioned as the hydrophobic phase (oils): paraffin oils, silicone oils, natural vegetable oils such as sesame seed oil, almond oil, castor oil, synthetic triglycerides such as caprylic/capric acid biglyceride, triglyceride mixture with vegetable fatty acids of chain length $C_{8-12}$ or with other specifically selected natural fatty acids, partial glyceride mixtures of saturated or unsaturated fatty acids which may also contain hydroxyl groups, and mono- and diglycerides of the $C_8/C_{10}$-fatty acids.

Fatty acid esters such as ethyl stearate, di-n-butyryl adipate, hexyl laurate, dipropylene glycol pelargonate, esters of a branched fatty acid of medium chain length with saturated fatty alcohols of chain length $C_{16}$–$C_{18}$, isopropyl myristate, isopropyl palmitate, caprylic/capric esters of saturated fatty alcohols of chain length $C_{12}$–$C_{18}$, isopropyl stearate, oleyl oleate, decyl oleate, ethyl oleate, ethyl lactate, waxy fatty acid esters such as artificial preen gland fat from ducks, dibutyl phthalate, diisopropyl adipate, ester mixtures related to the latter, etc.

Fatty alcohols such as isotridecyl alcohol, 2-octyldodecanol, cetylstearyl alcohol, oleyl alcohol.

Fatty acids such as, for example, oleic acid and its mixtures.

The following may be mentioned as hydrophilic phase: water, alcohols such as, for example, propylene glycol, glycerol, sorbitol and their mixtures.

The following may be mentioned as emulsifiers: non-ionic surfactants, for example polyoxyethylated castor oil, polyoxyethylated sorbitan monooleate, sorbitan monostearate, glycerol monostearate, polyoxyethyl stearate, alkylphenol polyglycol ethers;

ampholytic surfactants such as disodium N-lauryl-β-iminodipropionate or lecithin;

anionic surfactants such as sodium lauryl sulphate, fatty alcohol ether sulphates, the monoethynolamine salt of mono/dialkyl polyglycol ether orthophosphoric esters.

The following may be mentioned as further adjuvants: viscosity-increasing substances and substances which stabilise the emulsion, such as carboxymethylcellulose, methylcellulose and other cellulose and starch derivatives, polyacrylates, alginates, gelatine, gum arabic, polyvinylpyrrolidone, polyvinyl alcohol, copolymers of methyl vinyl ether and maleic anhydride, polyethylene glycols, waxes, colloidal silica, or mixtures of the substances mentioned.

Suspensions can he administered orally, dermally or in the form of injection. They are prepared by suspending the active substance in an excipient liquid, if appropriate with the addition of further adjuvants such as wetting agents, colourants, absorption accelerators, preservatives, antioxidants light stabilizers.

Excipient liquids which may be mentioned are all homogeneous solvents and solvent mixtures.

Wetting agents (dispersants) which may be mentioned are the surfactants indicated further above.

Further adjuvants which may be mentioned are those indicated further above.

Semi-solid preparations can be administered orally or dermally. They are only distinguished from the above-described suspensions and emulsions by their higher viscosity.

To prepare solid preparations, the active compound is mixed with suitable excipients, if appropriate with the addition of adjuvants, and the mixture is formulated as desired.

Excipients which may be mentioned are all physiologically acceptable solid inert substances. Suitable as such are inorganic and organic substances. Examples of inorganic substances are sodium chloride, carbonates such as calcium carbonate, hydrogencarbonates, aluminium oxides, silicas, clays, precipitated or colloidal silica, and phosphates.

Examples of organic substances are sugars, cellulose, foods and animal feeds such as dried milk, carcass meals, cereal meals and coarse cereal meals and starches.

Adjuvants are preservatives, antioxidants and colourants which have already been indicated further above.

Other suitable adjuvants are lubricants and glidants such as, for example, magnesium stearate, stearic acid, talc, bentonites, disintegrants such as starch or crosslinked polyvinylpyrrolidone, binders such as, for example, starch, gelatine or linear polyvinylpyrrolidone, and also dry binders such as microcrystalline cellulose.

In the preparations, the active compounds can also be present in the form of a mixture with synergists or with other active compounds which act against pathogenic endoparasites. Examples of such active compounds are L-2,3,5,6-tetrahydro-6-phenylimidazothiazole, benzimidazole carbonates, praziquantel, pyrantel, febantel.

Ready-to-use preparations contain the active compound in concentrations of 10 ppm—20 percent by weight, preferably of 0.1–10 percent by weight.

Preparations which are diluted prior to administration contain the active compound in concentrations of 0.5–90% by weight, preferably of 5–50% by weight.

In general, it has proved advantageous to administer amounts of approximately 1 to approximately 100 mg of active compound per kg of body weight per day, to achieve effective results.

EXAMPLE A

In vivo nematode test

Haemonchus contortus/sheep

Sheep which have been infected experimentally with Haemonchus contortus were treated after the prepatent time of the parasite had elapsed. The active compounds were administered orally and/or intravenously in the form of the pure active compound.

The degree of effectiveness is determined by quantitatively determining the nematode eggs excreted with the faeces before and after the treatment.

If egg excretion stops completely after the treatment, this means that the nematodes were aborted or are damaged to such an extent that they no longer produce eggs (dosis effectiva).

Active compounds which have been tested and effective dosages (dosis effectiva) can be seen from the table which follows:

| Active compound Example No. | Dosis effective in mg/kg |
| --- | --- |
| 1 | 10 |
| 2 | 10 |
| 4 | 10 |
| 5 | 10 |
| 11 | 10 |

PREPARATION EXAMPLES

1) Preparation of the compounds of the formula (I) in accordance with process 2

BOP-Cl (0.124 mmol) was added at 0° C. to a solution of compound II (0.104 mmol) and Hünig's base (0.258 mmol) in dichloromethane (100 ml), and stirring was continued for 24 hours at room temperature. After this period, the same amounts of BOP-Cl and base were added, and stirring was continued for a further 24 hours. The solution was washed twice using saturated sodium hydrogencarbonate solution, dried over sodium sulphate and concentrated. The residue was purified by column chromatography using toluene/ethyl acetate 5:1 as the eluent.

Compounds of the formula (I) were obtained in which the substituents have the following meaning:

TABLE 1

In this table and those which follow, the following abbreviations, whose meanings are indicated, are used:
Me — methyl
Et — ethyl
$^n$Pr — n-propyl
$^i$Bu — iso-butyl
$^s$Bu — sec-butyl
Bn — benzyl

| Ex. No. | $R^1$ | $R^2$ | $R^3$ | $R^4$ | $R^5$ | $R^6$ | FAB-MS M/Z (%) |
|---|---|---|---|---|---|---|---|
| 1 | Me | $^i$Bu | Me | Me | $^i$Bu | Me | 399 (M + H, 48) |
| 2 | Me | $^i$Bu | H | Me | $^i$Bu | H | 371 (M + H, 15) |
| 3 | Et | $^i$Bu | Me | Et | $^i$Bu | Bn | 503 (M + H, 34) |
| 4 | Me | $^n$Propyl | Me | Me | $^n$Propyl | Me | 371 (M + H, 50) |
| 5 | Me | $^s$Butyl | Me | Me | $^s$Butyl | Me | 399 (M + H, 100) |
| 6 | Me | $^n$Propyl | Me | Me | $^n$Propyl | Bn | 447 (M + H, 20) |
| 7 | Me | $^i$Bu | Me | Me | $^i$Bu | Bn | 475 (M + H, 100) |
| 8 | $^n$Pr | $^i$Bu | Me | $^n$Pr | $^i$Bu | Bn | 531 (M + H, 100) |
| 9 | Me | $^i$Bu | Me | Me | $^i$Bu | —CH$_2$-(3-Cl-phenyl) | 509 (M + H, 45) |
| 10 | Me | $^i$Bu | Me | Me | $^i$Bu | —CH$_2$-(2-Cl-phenyl) | 509 (M + H, 100) |
| 11 | Me | $^i$Bu | Me | Me | $^i$Bu | —CH$_2$-(4-Cl-phenyl) | 509 (M + H, 100) |

2a) Preparation of the compounds of the formula (II) in accordance with process 5a HCl gas was passed for 1.5 hours at 0° C. into a solution of the tert-butyl ester of the formula (III) (1.61 mmol) in dichloromethane (40 ml). The mixture was subsequently allowed to warm to room temperature, and stirring was continued for 12 hours. The solution was evaporated on a rotary evaporator and dried under a high vacuum. The residue was dissolved in water and the solution was added dropwise to a suspension of a basic ion exchanger (0.60 g) in 5 ml of water, the suspension was stirred for 3 hours and filtered and the filtrate was concentrated. After drying under a high vacuum, the product was reacted further without additional purification.

In accordance with this protocol, compounds of the formula (II) in which the substituents have the following meaning were obtained:

TABLE 2

| Ex. No. | $R^1$ | $R^2$ | $R^3$ | $R^4$ | $R^5$ | $R^6$ |
|---|---|---|---|---|---|---|
| II-1 | Me | $^i$Bu | Me | Me | $^i$Bu | Me |
| II-2 | Me | $^i$Bu | H | Me | $^i$Bu | H |
| II-3 | Et | $^i$Bu | Me | Et | $^i$Bu | Bn |
| II-4 | Me | $^n$Pr | Me | Me | $^n$Pr | Me |
| II-5 | Me | $^s$Bu | Me | Me | $^s$Bu | Me |
| II-6 | Me | $^n$Pr | Me | Me | $^n$Pr | Bn |
| II-7 | Me | $^i$Bu | Me | Me | $^i$Bu | Bn |
| II-8 | $^n$Pr | $^i$Bu | Me | $^n$Pr | $^i$Bu | Bn |

TABLE 2-continued

| Ex. No. | $R^1$ | $R^2$ | $R^3$ | $R^4$ | $R^5$ | $R^6$ |
|---|---|---|---|---|---|---|
| II-9 | Me | $^i$Bu | Me | Me | $^i$Bu | CH$_2$-(3-Cl-phenyl) |
| II-10 | Me | $^i$Bu | Me | Me | $^i$Bu | CH$_2$-(2-Cl-phenyl) |
| 11-11 | Me | $^i$Bu | Me | Me | $^i$Bu | CH$_2$-(4-Cl-phenyl) |

2b) Preparation of the compounds of the formula (II) in accordance with process 5b A solution of a compound of the formula (IV) (1.22 mmol) in dioxane (50 ml) was hydrogenated in the presence of Pd(OH)$_2$/C (20%; 200 mg) until the uptake of hydrogen had ceased (approximately 2 hours). After removal of the catalyst by filtration, compound (II) was obtained in virtually quantitative yield and was reacted further without additional purification.

3) Preparation of the compounds of the formula (III) in accordance with process 7

A solution of a compound of the formula (V) (1.22 mmol) in dioxane (50 ml) was hydrogenated in the presence of Pd(OH)$_2$/C (20%; 200 mg) until the uptake of hydrogen had ceased (approximately 2 hours). After removal of the catalyst by filtration, compound (III) was obtained in virtually quantitative yield and reacted further without additional purification.

In accordance with this protocol, compounds of the formula (III) in which the substituents have the following meaning were obtained:

dichloromethane (40 ml). The mixture was subsequently allowed to warm to room temperature, and stirring was continued for 12 hours. The solution was evaporated on a rotary evaporator and dried under a high vacuum. The residue was dissolved in water and the solution was added dropwise to a suspension of a basic ion exchanger (0.60 g) in 5 ml of water, the suspension was stirred for 3 hours and filtered and the filtrate was concentrated. After drying under a high vacuum, the product was reacted without further purification.

TABLE 3

| Ex. No. | $R^1$ | $R^2$ | $R^3$ | $R^4$ | $R^5$ | $R^6$ | A |
|---|---|---|---|---|---|---|---|
| III-1 | Me | $^i$Bu | Me | Me | $^i$Bu | Me | $^t$Bu |
| III-2 | Me | $^i$Bu | H | Me | $^i$Bu | H | $^t$Bu |
| III-3 | Et | $^i$Bu | Me | Et | $^i$Bu | Bn | $^t$Bu |
| III-4 | Me | $^n$Pr | Me | Me | $^n$Pr | Me | $^t$Bu |
| III-5 | Me | $^n$Bu | Me | Me | $^n$Bu | Me | $^t$Bu |
| III-6 | Me | $^n$Pr | Me | Me | $^n$Pr | Bn | $^t$Bu |
| III-7 | Me | $^i$Bu | Me | Me | $^i$Bu | Bn | $^t$Bu |
| III-8 | $^n$Pr | $^i$Bu | Me | $^n$Pr | $^i$Bu | Bn | $^t$Bu |
| III-9 | Me | $^i$Bu | Me | Me | $^i$Bu | 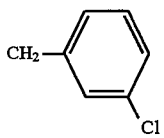 | $^t$Bu |
| III-10 | Me | $^i$Bu | Me | Me | $^i$Bu | 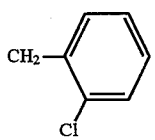 | $^t$Bu |
| III-11 | Me | $^i$Bu | Me | Me | $^i$Bu | 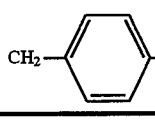 | $^t$Bu |

4. Preparation of the compounds of the formula (IV) in accordance with process 9

HCl gas was passed for 1.5 hours at 0° C. into a solution of the tert-butyl ester of the formula (V) (1.70 mmol) in In accordance with this protocol, compounds of the formula (IV) in which the substituents have the following meaning were obtained:

TABLE 4

Preparation of the compounds (IV)

| Ex. No. | $R^1$ | $R^2$ | $R^3$ | $R^4$ | $R^5$ | $R^6$ | B |
|---|---|---|---|---|---|---|---|
| IV-1 | Me | $^i$Bu | Me | Me | $^i$Bu | Me | Bn |
| IV-2 | Me | $^i$Bu | H | Me | $^i$Bu | H | Bn |
| IV-3 | Et | $^i$Bu | Me | Et | $^i$Bu | Bn | Bn |
| IV-4 | Me | $^n$Pr | Me | Me | $^n$Pr | Me | Bn |
| IV-5 | Me | $^n$Bu | Me | Me | $^n$Bu | Me | Bn |
| IV-6 | Me | $^n$Pr | Me | Me | $^n$Pr | Bn | Bn |
| IV-7 | Me | $^i$Bu | Me | Me | $^i$Bu | Bn | Bn |
| IV-8 | $^n$Pr | $^i$Bu | Me | $^n$Pr | $^i$Bu | Bn | Bn |
| IV-9 | Me | $^i$Bu | Me | Me | $^i$Bu | 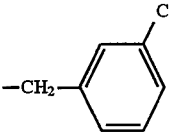 | Bn |

TABLE 4-continued

Preparation of the compounds (IV)

| Ex. No. | R¹ | R² | R³ | R⁴ | R⁵ | R⁶ | B |
|---|---|---|---|---|---|---|---|
| IV-10 | Me | $^i$Bu | Me | Me | $^i$Bu | —CH$_2$—C$_6$H$_4$—Cl (2-Cl) | Bn |
| IV-11 | Me | $^i$Bu | Me | Me | $^i$Bu | —CH$_2$—C$_6$H$_4$—Cl (4-Cl) | Bn |

5. Preparation of the compounds of the formula (V) in accordance with process 11

Didepsipeptides of the formula (VI) (2.50 mmol) were introduced into dichloromethane (15 ml), and ethyldiisopropylamine (0.91 mmol) and BoP-Cl (0.44 mmol) were added to the solution which was cooled to 0° C. Didepsipeptides of the formula (VII) (2.50 mmol) in dichloromethane (15 ml) were added dropwise. Stirring was continued for 3 hours at 0° C. and for 18 hours at room temperature; the mixture was then diluted with dichloromethane, washed in succession using 2N hydrochloric acid and saturated sodium hydrogencarbonate solution, dried over sodium sulphate and concentrated. Compounds of the formula (V) were reacted further without additional purification.

In accordance with this protocol, the compounds of the formula (V) which are compiled in Table 5 below were obtained:

6. Preparation of the compounds of the formula (VI) in accordance with process 13

HCl gas was passed for 2 hours at 0° C. into a solution of the didepsipeptide of the formula (VIII) (2.90 mmol) in dichloromethane (50 ml).

Stirring was then continued for 8 hours at room temperature, and the product was concentrated and dried under a high vacuum. The residue was dissolved in water and the solution was added dropwise to a suspension of a basic ion exchanger (1.10 g) in 10 ml of water, the suspension was stirred for 3 hours and filtered and the filtrate was concentrated. After drying under a high vacuum, the product was reacted further without additional purification.

In accordance with this protocol, the following compounds of the formula (VI) in which the substituents have the following meaning were obtained:

TABLE 5

| Ex. No. | R¹ | R² | R³ | R⁴ | R⁵ | R⁶ | A | B |
|---|---|---|---|---|---|---|---|---|
| V-1 | Me | $^i$Bu | Me | Me | $^i$Bu | Me | $^t$Bu | Bn |
| V-2 | Me | $^i$Bu | H | Me | $^i$Bu | H | $^t$Bu | Bn |
| V-3 | Et | $^i$Bu | Me | Et | $^i$Bu | Bn | $^t$Bu | Bn |
| V-4 | Me | $^n$Pr | Me | Me | $^n$Pr | Me | $^t$Bu | Bn |
| V-5 | Me | $^s$Bu | Me | Me | $^s$Bu | Me | $^t$Bu | Bn |
| V-6 | Me | $^n$Pr | Me | Me | $^n$Pr | Bn | $^t$Bu | Bn |
| V-7 | Me | $^i$Bu | Me | Me | $^i$Bu | Bn | $^t$Bu | Bn |
| V-8 | $^n$Pr | $^i$Bu | Me | $^n$Pr | $^i$Bu | Bn | $^t$Bu | Bn |
| V-9 | Me | $^i$Bu | Me | Me | $^i$Bu | —CH$_2$—C$_6$H$_4$—Cl (2-Cl) | $^t$Bu | Bn |
| V-10 | Me | $^i$Bu | Me | Me | $^i$Bu | —CH$_2$—C$_6$H$_4$—Cl (3-Cl) | $^t$Bu | Bn |
| V-11 | Me | $^i$Bu | Me | Me | $^i$Bu | —CH$_2$—C$_6$H$_4$—Cl (4-Cl) | $^t$Bu | Bn |

TABLE 6

| Ex. No. | R$^1$ | R$^2$ | R$^3$ | Z | B |
|---|---|---|---|---|---|
| VI-1 | Me | $^i$Bu | Me | OH | Bn |
| VI-2 | Me | $^i$Bu | H | OH | Bn |
| VI-3 | Et | $^i$Bu | Me | OH | Bn |
| VI-4 | Me | $^n$Pr | Me | OH | Bn |
| VI-5 | Me | $^s$Bu | Me | OH | Bn |
| VI-6 | $^n$Pr | $^i$Bu | Me | OH | Bn |

7. Preparation of the compounds of the formula (VII) in accordance with process 15.

A solution of a compound of the formula (IX) (9.50 mmol) in dioxane (50 ml) was hydrogenated in the presence of Pd(OH)$_2$/C (20%; 600 mg) until the uptake of hydrogen had ceased (approximately 2 hours). After removal of the catalyst by filtration, compound (VII) was obtained in virtually quantitative yield and was reacted further without additional purification.

In accordance with this protocol, compounds of the formula (VII) in which the substituents have the following meaning were obtained:

TABLE 7

| Ex. No. | R$^4$ | R$^5$ | R$^6$ | A | D |
|---|---|---|---|---|---|
| VII-1 | Me | $^i$Bu | Me | H | $^t$Bu |
| VII-2 | Me | $^i$Bu | H | H | $^t$Bu |
| VII-3 | Et | $^i$Bu | Bn | H | $^t$Bu |
| VII-4 | Me | $^n$Pr | Me | H | $^t$Bu |
| VII-5 | Me | $^s$Bu | Me | H | $^t$Bu |
| VII-6 | Me | $^n$Pr | Bn | H | $^t$Bu |
| VII-7 | Me | $^i$Bu | Bn | H | $^t$Bu |
| VII-8 | $^n$Pr | $^i$Bu | Bn | H | $^t$Bu |
| VII-9 | Me | $^i$Bu | CH$_2$-(3-Cl-C$_6$H$_4$) | H | $^t$Bu |
| VII-10 | Me | $^i$Bu | CH$_2$-(3,5-Cl$_2$-C$_6$H$_3$) | H | $^t$Bu |
| VII-11 | Me | $^i$Bu | CH$_2$-(4-Cl-C$_6$H$_4$) | H | $^t$Bu |

8. Preparation of the compounds of the formula (VIII) in accordance with process 17

The amino acid of the formula (X) (0.40 mol) was dissolved in 1400 ml of ethanol and 800 ml of water, a 20% (weight/volume) caesium carbonate aqueous solution (390 ml) was added, and the mixture was stirred for 2 hours at room temperature. It was subsequently concentrated, dissolved in water (2000 ml) and freeze-dried. 0.40 ml of this caesium salt were introduced into 1000 ml of dimethylformamide, 0.40 mol of the chloro carboxylic acid of the formula (XI) were added at room temperature, and the mixture was stirred for 20 hours at room temperature. The solution was concentrated, the residue was poured into water (1000 ml), the mixture was extracted four times using ethyl acetate, and the extract was dried over sodium sulphate and concentrated. The residue was reacted further without additional purification.

Analogously, the compounds of the formula (VIII) in which the substituents have the following meaning were obtained:

TABLE 8

| Ex. No. | R$^1$ | R$^2$ | R$^3$ | A | B |
|---|---|---|---|---|---|
| VIII-1 | Me | $^i$Bu | Me | $^t$Bu | Bn |
| VIII-2 | Me | $^i$Bu | H | $^t$Bu | Bn |
| VIII-3 | Et | $^i$Bu | Me | $^t$Bu | Bn |
| VIII-4 | Me | $^n$Pr | Me | $^t$Bu | Bn |
| VIII-5 | Me | $^s$Bu | Me | $^t$Bu | Bn |
| VIII-6 | $^n$Pr | $^i$Bu | Me | $^t$Bu | Bn |

9. Preparation of the compounds of the formula (IX) in accordance with process 19

The amino acid of the formula (XII) (0.40 mol) was dissolved in 1400 ml of ethanol and 800 ml of water, a 20% (weight/volume) caesium carbonate aqueous solution (390 ml) was added, and the mixture was stirred for 2 hours at room temperature. It was subsequently concentrated, dissolved in water (2000 ml) and freeze-dried. 0.40 mol of this caesium salt was introduced into 100 ml of dimethylformamide, 0.40 mol of the chloro carboxylic acid of the formula (XIII) were added at room temperature, and the mixture was stirred for 20 hours at room temperature. The solution was concentrated, the residue was poured into water (1000 ml), the mixture was extracted four times using ethyl acetate, and the extract was dried over sodium sulphate and concentrated. The residue was reacted further without additional purification.

Analogously, the compounds of the formula (IX) in which the substituents have the following meaning were obtained:

TABLE 9

| Ex. No. | R$^4$ | R$^5$ | R$^6$ | B | A |
|---|---|---|---|---|---|
| VII-1 | Me | $^i$Bu | Me | Bn | $^t$Bu |
| VII-2 | Me | $^i$Bu | H | Bn | $^t$Bu |
| VII-3 | Et | $^i$Bu | Bn | Bn | $^t$Bu |
| VII-4 | Me | $^n$Pr | Me | Bn | $^t$Bu |
| VII-5 | Me | $^s$Bu | Me | Bn | $^t$Bu |
| VII-6 | Me | $^n$Pr | Bn | Bn | $^t$Bu |
| VII-7 | Me | $^i$Bu | Bn | Bn | $^t$Bu |
| VII-8 | $^n$Pr | $^i$Bu | Bn | Bn | $^t$Bu |
| VII-9 | Me | $^i$Bu | CH$_2$-(3-Cl-C$_6$H$_4$) | Bn | $^t$Bu |
| VII-10 | Me | $^i$Bu | CH$_2$-(3,5-Cl$_2$-C$_6$H$_3$) | Bn | $^t$Bu |
| VII-10 | Me | $^i$Bu | CH$_2$-(4-Cl-C$_6$H$_4$) | Bn | $^t$Bu |

We claim:

1. A method for combating endoparasites in human or animals which comprises administering to said humans or animals an endoparasitically effective amount of a cyclic depsipeptide of the formula (I):

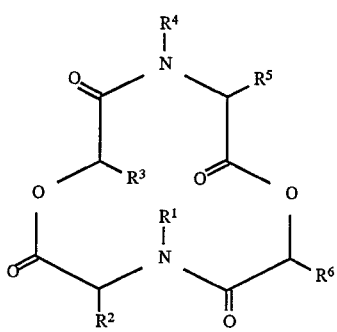

in which
- $R^1$ and $R^4$ independently of one another represent hydrogen or represent straight-chain or branched alkyl, cycloalkyl, aralkyl, aryl, heteroaryl, or heteroarylalkyl, each of which is optionally substituted by one or more substituents;
- $R^2$, $R^3$, $R^5$ and $R^6$ independently of one another represent hydrogen, straight-chain or branched alkyl having up to 8 carbon atoms, halogenoalkyl, hydroxyalkyl, alkanoyloxyalkyl, alkoxyalkyl, aryloxyalkyl, mercaptoalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, or guanidinoalkyl which is optionally substituted by one or two benzyloxycarbonyl radicals or by one, two, three or four alkyl radicals, or alkoxycarbonylaminoalkyl, 9-fluorenylmethoxycarbonyl(Fmoc)aminoalkyl, alkenyl, cycloalkyl, cycloalkylalkyl, or represent aryl, arylalkyl, heteroaryl or heteroarylalkyl, each of which is optionally substituted by one or more substituents;
  wherein, except as otherwise indicated, the substituents for $R^{1-6}$ are identical or different and are selected from the group consisting of alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, the halogen atoms being identical or different, hydroxyl, halogen, cyano, nitro, amino, monoalkyl- and dialkylamino having 1 to 4 carbon atoms per alkyl group, acyl radicals, alkylsulphinyl having 1 to 4 carbon atoms, halogenalkylsulphinyl having 1 to 4 carbon atoms and 1 to 5 halogen atoms, the halogen atoms being identical or different, $SO_3H$, alkylsulphonyl having 1 to 4 carbon atoms, halogenoalkylsulphonyl having 1 to 4 carbon atoms and 1 to 5 halogen atoms, arylsulphonyl having 6 or 10 aryl carbon atoms, aryl, aryloxy, heteroaryl, heteroaryloxy, each of which can have one of the aforementioned substituents, and the forminino radical (—CH=N—O-alkyl);

or an optical isomer thereof or a racemic mixture thereof.

2. The method according to claim 1, wherein in said cyclic depsipeptide of the formula (I):
$R^1$ and $R^4$ independently of one another represent hydrogen, or straight-chain or branched $C_{1-8}$-alkyl, 1-5-halogen-$C_{1-4}$-alkyl, hydroxy-$C_{1-6}$-alkyl, $C_{1-4}$-alkanoyloxy-$C_{1-6}$-alkyl, $C_{1-4}$-alkoxy-$C_{1-6}$-alkyl, aryl-$C_{1-4}$-alkyloxy-$C_{1-6}$-alkyl, mercapto-$C_{1-6}$-alkyl, $C_{1-4}$-alkylthio-$C_{1-6}$-alkyl, $C_{1-4}$-alkylsulphinyl-$C_{1-6}$-alkyl, $C_{1-4}$-alkylsulphonyl-$C_{1-6}$-alkyl, carboxy-$C_{1-6}$-alkyl, $C_{1-4}$-alkoxycarbonyl-$C_{1-6}$-alkyl, aryl-$C_{1-4}$-alkoxycarbonyl-$C_{1-6}$-alkyl, carbamoyl-$C_{1-6}$-alkyl, amino-$C_{1-6}$-alkyl, $C_{1-4}$-alkylamino-$C_{1-6}$-alkyl, di-$C_{1-4}$-alkylamino-$C_{1-6}$-alkyl, guanidino-$C_{1-6}$-alkyl, $C_{1-4}$-alkoxycarbonylamino-$C_{1-6}$-alkyl, 9-fluorenylmethoxycarbonyl(Fmoc)amino-$C_{1-6}$-alkyl, $C_{3-7}$-cycloalkyl, $C_{3-7}$-cycloalkyl-$C_{1-4}$-alkyl, phenyl, or phenyl-$C_{1-4}$-alkyl, each of which is optionally substituted by one or more substituents independently selected from the group consisting of halogen, hydroxyl, nitro, cyano, $C_{1-4}$-alkoxy, and $C_{1-4}$-alkyl;

$R^2$, $R^3$, $R^5$ and $R^6$ independently of one another represent hydrogen, straight-chain or branched $C_{1-8}$-alkyl, 1-5-halogen-$C_{1-4}$-alkyl, hydroxy-$C_{1-6}$-alkyl, $C_{1-4}$-alkanoyloxy-$C_{1-6}$-alkyl, $C_{1-4}$-alkoxy-$C_{1-6}$-alkyl, aryl-$C_{1-4}$-alkyloxy-$C_{1-6}$-alkyl, mercapto-$C_{1-6}$-alkyl, $C_{1-4}$-alkylthio-$C_{1-6}$-alkyl, $C_{1-4}$-alkylsulphinyl-$C_{1-6}$-alkyl, $C_{1-4}$-alkylsulphonyl-$C_{1-6}$-alkyl, carboxy-$C_{1-6}$-alkyl, $C_{1-4}$-alkoxycarbonyl-$C_{1-6}$-alkyl, aryl-$C_{1-4}$-alkoxycarbonyl-$C_{1-6}$-alkyl, carbamoyl-$C_{1-6}$-alkyl, amino-$C_{1-6}$-alkyl, $C_{1-4}$-alkylamino-$C_{1-6}$-alkyl, di-$C_{1-4}$-alkylamino-$C_{1-6}$-alkyl, $C_{2-8}$-alkenyl, $C_{3-7}$-cycloalkyl, or $C_{3-7}$-cycloalkyl-$C_{1-4}$-alkyl, or phenyl, phenyl-$C_{1-4}$-alkyl, thienylmethyl, or pyridylmethyl, each of which is optionally substituted by one or more substituents independently selected from the group consisting of halogen, hydroxyl, $SO_3H$, cyano, nitro, amino, di-$C_{1-4}$-alkylamino, $C_{1-4}$-alkoxy, and $C_{1-4}$-alkyl.

3. The method according to claim 1, wherein in said cyclic depsipeptide of the formula (I):
$R^1$ and $R^4$ independently of one another represent hydrogen, or straight-chain or branched $C_{1-8}$-alkyl, 1-5-halogen-$C_{1-4}$-alkyl, hydroxy-$C_{1-6}$-alkyl, $C_{1-4}$-alkanoyloxy-$C_{1-6}$-alkyl, $C_{1-4}$-alkoxy-$C_{1-6}$-alkyl, aryl-$C_{1-4}$-alkyloxy-$C_{1-6}$-alkyl, $C_{1-4}$-alkoxycarbonylamino-$C_{1-6}$-alkyl, $C_{3-7}$-cycloalkyl, $C_{3-7}$-cycloalkyl-$C_{1-4}$-alkyl, or phenyl-$C_{1-4}$-alkyl, each of which is optionally substituted by one or more substituents independently selected from the group consisting of halogen, hydroxyl, nitro, cyano, $C_{1-4}$-alkoxy, and $C_{1-4}$-alkyl;

$R^2$, $R^3$, $R^5$ and $R^6$ independently of one another represent hydrogen, straight-chain or branched $C_{1-8}$-alkyl, 1-5-halogen-$C_{1-4}$-alkyl, hydroxy-$C_{1-6}$-alkyl, aryl-$C_{1-4}$-alkyloxy-$C_{1-6}$-alkyl, carboxy-$C_{1-6}$-alkyl, $C_{1-4}$-alkoxycarbonyl-$C_{1-6}$-alkyl, aryl-$C_{1-4}$-alkoxycarbonyl-$C_{1-6}$-alkyl, $C_{1-4}$-alkylamino-$C_{1-6}$-alkyl, di-$C_{1-4}$-alkylamino-$C_{1-6}$-alkyl, $C_{2-8}$-alkenyl, $C_{3-7}$-cycloalkyl, or $C_{3-7}$-cycloalkyl-$C_{1-4}$-alkyl, or phenyl, phenyl-$C_{1-4}$-alkyl, or thienylmethyl, each of which is optionally substituted by one or more substituents independently selected from the group consisting of halogen, hydroxyl, $SO_3H$, cyano, nitro, amino, di-$C_{1-4}$-alkylamino, $C_{1-4}$-alkoxy, and $C_{1-4}$-alkyl.

4. The method according to claim 1, wherein in said cyclic depsipeptide of the formula (I):
$R^1$ and $R^4$ independently of one another represent hydrogen, or straight-chain or branched $C_{1-8}$-alkyl, $C_{3-7}$-cycloalkyl-$C_{1-4}$-alkyl, or phenyl-$C_{1-4}$-alkyl;

$R^2$, $R^3$, $R^5$ and $R^6$ independently of one another represent hydrogen, straight-chain or branched $C_{1-8}$-alkyl, 1-5-halogen-$C_{1-4}$-alkyl, $C_{2-8}$-alkenyl, $C_{3-7}$-cycloalkyl, or $C_{3-7}$-cycloalkyl-$C_{1-4}$-alkyl, or phenyl-$C_{1-4}$-alkyl, or thienylmethyl, each of which is optionally substituted by one or more substituents independently selected from the group consisting of halogen, hydroxyl, $SO_3H$, cyano, nitro, amino, di-$C_{1-4}$-alkylamino, $C_{1-4}$-alkoxy, and $C_{1-4}$-alkyl.

5. The method according to claim 1, wherein in the cyclic depsipeptide of formula (I):

| $R^1$ is: | $R^2$ is: | $R^3$ is: | $R^4$ is: | $R^5$ is: | $R^6$ is: |
|---|---|---|---|---|---|
| —CHMeCH$_2$Me | —Cyclohexyl | —CHMeCH$_2$Me | —Me | —CHMeCH$_2$Me | —Me |
| —CHMeCH$_2$Me | —Cyclohexyl | —CHMeCH$_2$Me | —Me | —CHMeCH$_2$Me | —Cyclohexyl |
| —CHMeCH$_2$Me | —CH$_2$—Phe | —CHMeCH$_2$Me | —Me | —CHMeCH$_2$Me | —Me |
| —CHMeCH$_2$Me | —CH$_2$—Phe | —CHMeCH$_2$Me | —Me | —CHMeCH$_2$Me | —CH$_2$—Phe |
| —CHMeCH$_2$Me | —(CH$_2$)$_3$—Me | —CHMeCH$_2$Me | —Me | —CHMeCH$_2$Me | —Me |
| —CHMeCH$_2$Me | —(CH$_2$)$_3$—Me | —CHMeCH$_2$Me | —Me | —CHMeCH$_2$Me | —(CH$_2$)$_3$—Me |
| —CHMe$_2$ | —CH$_2$—Phe | —CHMeCH$_2$Me | —Me | —CHMeCH$_2$Me | —Me |
| —CH$_2$—Phe | —CHMe$_2$ | —CH$_2$—Phe | —CHMe$_2$ | —CHMeCH$_2$Me | —CHMe$_2$ |
| —CH$_2$CHMe$_2$ | —CH$_2$—Phe | —CH$_2$CHMe$_2$ | —Me | —CH$_2$CHMe$_2$ | —CH$_2$—Phe |
| —(CH$_2$)$_3$—Me | —Me | —CHMeCH$_2$Me | —Me | —CHMeCH$_2$Me | —Me |
| —CHMe$_2$ | —Me | —CHMe$_2$ | —Me | —CHMe$_2$ | —Me |
| —CH$_2$—Me | —Me | —CH$_2$—Me | —Me | —CH$_2$—Me | —Me |
| —(CH$_2$)$_2$—Me | —Me | —(CH$_2$)$_2$—Me | —Me | —(CH$_2$)$_2$—Me | —Me |
| —(CH$_2$)$_3$—Me | —Me | —(CH$_2$)$_3$—Me | —Me | —(CH$_2$)$_3$—Me | —Me |
| —CH$_2$—CH=CH$_2$ | —Me | —CH$_2$—CH=CH$_2$ | —Me | —(CH$_2$)—CH=CH$_2$ | —Me |
| —CHMeCH$_2$Me | —Me | —CHMeCH$_2$Me | —Me | —CHMeCH$_2$Me | —CH$_2$—Me |
| —CHMeCH$_2$Me | —Me | —CHMeCH$_2$Me | —Me | —CHMeCH$_2$Me | —(CH$_2$)$_2$—Me |
| —CHMeCH$_2$Me | —Me | —CHMeCH$_2$Me | —Me | —CHMeCH$_2$Me | —(CH$_2$)$_3$—Me |
| —CHMeCH$_2$Me | —Me | —CHMeCH$_2$Me | —Me | —CH$_2$Me | —Me |
| —CHMeCH$_2$Me | —Me | —CHMeCH$_2$Me | —Me | —(CH$_2$)$_2$—Me | —Me |
| —Cyclohexyl | —Me | —Cyclohexyl | —Me | —Cyclohexyl | —Me |
| —CH$_2$CHMe$_2$ | —Cyclohexyl | —CH$_2$CHMe$_2$ | —Me | —CH$_2$CHMe$_2$ | —Cyclohexyl |
| —CH$_2$CHMe$_2$ | —Cyclohexyl | —CH$_2$CHMe$_2$ | —Me | —CH$_2$CHMe$_2$ | —Me |
| —CHMeCH$_2$Me | —CHMe$_2$ | —CHMeCH$_2$Me | —CHMe$_2$ | —CHMeCH$_2$Me | —Me |
| —CH$_2$—Phe | —Me | —CH$_2$—Phe | —Me | —CH$_2$—Phe | —Me |
| —Cyclohexyl | —Me | —Cyclohexyl | —Me | —Cyclohexyl | —Me |
| —CHMe$_2$ | —CHMe$_2$ | —CHMe$_2$ | —Me | —CHMe$_2$ | —Me |
| —CHMe$_2$ | —CHMe$_2$ | —CHMe$_2$ | —CHMe$_2$ | —CHMe$_2$ | —Me |
| —CH$_2$—Me | —CHMe$_2$ | —CH$_2$Me | —Me | —CH$_2$—Me | —Me |
| —CH$_2$—Me | —CHMe$_2$ | —CH$_2$Me | —CHMe$_2$ | —CH$_2$—Me | —Me |
| —(CH$_2$)$_2$—Me | —CHMe$_2$ | —(CH$_2$)$_2$—Me | —Me | —(CH$_2$)$_2$—Me | —Me |
| —(CH$_2$)$_2$—Me | —CHMe$_2$ | —(CH$_2$)$_2$—Me | —CHMe$_2$ | —(CH$_2$)$_2$—Me | —Me |
| —(CH$_2$)$_3$—Me | —CHMe$_2$ | —(CH$_2$)$_3$—Me | —Me | —(CH$_2$)$_3$—Me | —Me |
| —(CH$_2$)$_3$—Me | —CHMe$_2$ | —(CH$_2$)$_3$—Me | —CHMe$_2$ | —(CH$_2$)$_3$—Me | —Me |
| —CH$_2$—CH=CH$_2$ | —CHMe$_2$ | —CH$_2$—CH=CH$_2$ | —Me | —CH$_2$—CH=CH$_2$ | —Me |
| —CH$_2$—CH=CH$_2$ | —CHMe$_2$ | —CH$_2$—CH=CH$_2$ | —CHMe$_2$ | —CH$_2$—CH=CH$_2$ | —Me |
| —Me | —CH$_2$CHMe$_2$ | Me | Me | —CH$_2$CHMe$_2$ | —CH$_2$—C$_6$H$_4$—NO$_2$ (para) |
| —Me | —CH$_2$CHMe$_2$ | Me | Me | —CH$_2$CHMe$_2$ | —CH$_2$—C$_6$H$_4$—NH$_2$ (para) |
| —Me | —CH$_2$CHMe$_2$ | Me | Me | —CH$_2$CHMe$_2$ | —CH$_2$—C$_6$H$_4$—NMe$_2$ (para) |
| —Me | —CH$_2$CHMe$_2$ | Me | Me | —CH$_2$CHMe$_2$ | —CH$_2$—C$_6$H$_4$—SO$_3$H (para) |
| —Me | —CH$_2$CHMe$_2$ | Me | Me | —CH$_2$CHMe$_2$ | —CH$_2$—(thienyl) | wherein
Me represents methyl; and
Phe represents phenyl.

6. An endoparasiticidal composition comprising a pharmaceutically acceptable carrier and an endoparasitically effective amount of a cyclic depsipeptide of the formula (I):

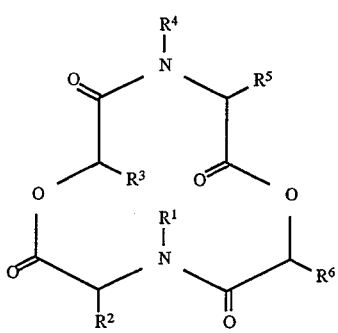

in which

R$^1$ and R$^4$ independently of one another represent hydrogen or represent straight-chain or branched alkyl, cycloalkyl, aralkyl, aryl, heteroaryl, or heteroarylalkyl, each of which is optionally substituted by one or more substituents;

R$^2$, R$^3$, R$^5$ and R$^6$ independently of one another represent hydrogen, straight-chain or branched alkyl having up to 8 carbon atoms, halogenoalkyl, hydroxyalkyl, alkanoyloxyalkyl, alkoxyalkyl, aryloxyalkyl, mercaptoalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, or guanidinoalkyl which is optionally substituted by one or two benzyloxycarbonyl radicals or by one, two, three or four alkyl radicals, or alkoxycarbonylaminoalkyl, 9-fluorenylmethoxycarbonyl(Fmoc)aminoalkyl, alkenyl, cycloalkyl, cycloalkylalkyl, or represent aryl, arylalkyl, heteroaryl or heteroarylalkyl, each of which is optionally substituted by one or more substituents; wherein, except as otherwise indicated, the substituents for R$^{1-6}$ are identical or different and are selected from the group consisting of alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, the halogen atoms being identical or different, hydroxyl, halogen, cyano, nitro, amino, monoalkyl- and dialkylamino having 1 to 4 carbon atoms per alkyl group, acyl radicals, alkylsulphinyl having 1 to 4 carbon atoms, halogenalkylsulphinyl having 1 to 4 carbon atoms and 1 to 5 halogen atoms, the halogen atoms being identical or different, SO$_3$H, alkylsulphonyl having 1 to 4 carbon atoms, halogenoalkylsulphonyl having 1 to 4 carbon atoms and 1 to 5 halogen atoms, arylsulphonyl having 6 or 10 aryl carbon atoms, aryl, aryloxy, heteroaryl, heteroaryloxy, each of which can have one of the aforementioned substituents, and the forminino radical (—CH=N—O-alkyl);

or an optical isomer thereof or a racemic mixture thereof.

7. The composition according to claim 6, wherein in said cyclic depsipeptide of the formula (I):

R$^1$ and R$^4$ independently of one another represent hydrogen, or straight-chain or branched C$_{1-8}$-alkyl, 1-5-halogen-C$_{1-4}$-alkyl, hydroxy-C$_{1-6}$-alkyl, C$_{1-4}$-alkanoyloxy-C$_{1-6}$-alkyl, C$_{1-4}$-alkoxy-C$_{1-6}$-alkyl, aryl-C$_{1-4}$-alkyloxy-C$_{1-6}$-alkyl, mercapto-C$_{1-6}$-alkyl, C$_{1-4}$-alkylthio-C$_{1-6}$-alkyl, C$_{1-4}$-alkylsulphinyl-C$_{1-6}$-alkyl, C$_{1-4}$-alkylsulphonyl-C$_{1-6}$-alkyl, carboxy-C$_{1-6}$-alkyl, C$_{1-4}$-alkoxycarbonyl-C$_{1-6}$-alkyl, aryl-C$_{1-4}$-alkoxycarbonyl-C$_{1-6}$-alkyl, carbamoyl-C$_{1-6}$-alkyl, amino-C$_{1-6}$-alkyl, C$_{1-4}$-alkylamino-C$_{1-6}$-alkyl, di-C$_{1-4}$-alkylamino-C$_{1-6}$-alkyl, guanidino-C$_{1-6}$-alkyl, C$_{1-4}$-alkoxycarbonylamino-C$_{1-6}$-alkyl, 9-fluorenylmethoxycarbonyl(Fmoc)amino-C$_{1-6}$-alkyl, C$_{3-7}$-cycloalkyl, C$_{3-7}$-cycloalkyl-C$_{1-4}$-alkyl, phenyl, or phenyl-C$_{1-4}$-alkyl, each of which is optionally substituted by one or more substituents independently selected from the group consisting of halogen, hydroxyl, nitro, cyano, C$_{1-4}$-alkoxy, and C$_{1-4}$-alkyl;

R$^2$, R$^3$, R$^5$ and R$^6$ independently of one another represent hydrogen, straight-chain or branched C$_{1-8}$-alkyl, 1-5-halogen-C$_{1-4}$-alkyl, hydroxy-C$_{1-6}$-alkyl, C$_{1-4}$-alkanoyloxy-C$_{1-6}$-alkyl, C$_{1-4}$-alkoxy-C$_{1-6}$-alkyl, aryl-C$_{1-4}$-alkyloxy-C$_{1-6}$-alkyl, mercapto-C$_{1-6}$-alkyl, C$_{1-4}$-alkylthio-C$_{1-6}$-alkyl, C$_{1-4}$-alkylsulphinyl-C$_{1-6}$-alkyl, C$_{1-4}$-alkylsulphonyl-C$_{1-6}$-alkyl, carboxy-C$_{1-6}$-alkyl, C$_{1-4}$-alkoxycarbonyl-C$_{1-6}$-alkyl, aryl-C$_{1-4}$-alkoxycarbonyl-C$_{1-6}$-alkyl, carbamoyl-C$_{1-6}$-alkyl, amino-C$_{1-6}$-alkyl, C$_{1-4}$-alkylamino -C$_{1-6}$-alkyl, di-C$_{1-4}$-alkylamino-C$_{1-6}$-alkyl, C$_{2-8}$-alkenyl, C$_{3-7}$-cycloalkyl or C$_{3-7}$-cycloalkyl-C$_{1-4}$-alkyl, or phenyl, phenyl-C$_{1-4}$-alkyl, thienylmethyl, or pyridylmethyl, each of which is optionally substituted by one or more substituents independently selected from the group consisting of halogen, hydroxyl, SO$_3$H, cyano, nitro, amino, di-C$_{1-4}$-alkylamino, C$_{1-4}$-alkoxy, and C$_{1-4}$-alkyl.

8. The composition according to claim 6, wherein said cyclic depsipeptide of the formula (I):

R$^1$ and R$^4$ independently of one another represent hydrogen, or straight-chain or branched C$_{1-8}$-alkyl, 1-5-halogen-C$_{1-4}$-alkyl, hydroxy-C$_{1-6}$-alkyl, C$_{1-4}$-alkanoyloxy-C$_{1-6}$-alkyl, C$_{1-4}$-alkoxy-C$_{1-6}$-alkyl, aryl-C$_{1-4}$-alkyloxy-C$_{1-6}$-alkyl, C$_{1-4}$-alkoxycarbonylamino-C$_{1-6}$-alkyl, C$_{3-7}$-cycloalkyl, C$_{3-7}$-cycloalkyl-C$_{1-4}$-alkyl, or phenyl-C$_{1-4}$-alkyl, each of which is optionally substituted by one or more substituents independently selected from the group consisting of halogen, hydroxyl, nitro, cyano, C$_{1-4}$-alkoxy, and C$_{1-4}$-alkyl;

R$^2$, R$^3$, R$^5$ and R$^6$ independently of one another represent hydrogen, straight-chain or branched C$_{1-8}$-alkyl, 1-5-halogen-C$_{1-4}$-alkyl, hydroxy-C$_{1-6}$-alkyl, aryl-C$_{1-4}$-alkyloxy-C$_{1-6}$-alkyl, carboxy-C$_{1-6}$-alkyl, C$_{1-4}$-alkoxycarbonyl-C$_{1-6}$-alkyl, aryl-C$_{1-4}$-alkoxycarbonyl-C$_{1-6}$-alkyl, C$_{1-4}$-alkylamino-C$_{1-6}$-alkyl, di-C$_{1-4}$-alkylamino-C$_{1-6}$-alkyl, C$_{2-8}$-alkenyl, C$_{3-7}$-cycloalkyl, or C$_{3-7}$-cycloalkyl-C$_{1-4}$-alkyl, or phenyl, phenyl-C$_{1-4}$-alkyl, or thienylmethyl, each of which is optionally substituted by one or more substituents independently selected from the group consisting of halogen, hydroxyl, SO$_3$H, cyano, nitro, amino, di-C$_{1-4}$-alkylamino, C$_{1-4}$-alkoxy, and C$_{1-4}$-alkyl.

9. The composition according to claim 6, wherein in said cyclic depsipeptide of the formula (I):

R$^1$ and R$^4$ independently of one another represent hydrogen, or straight-chain or branched C$_{1-8}$-alkyl, C$_{3-7}$-cycloalkyl-C$_{1-4}$-alkyl, or phenyl-C$_{1-4}$-alkyl;

R$^2$, R$^3$, R$^5$ and R$^6$ independently of one another represent hydrogen, straight-chain or branched C$_{1-8}$-alkyl, 1-5-halogen-C$_{1-4}$-alkyl, C$_{2-8}$-alkenyl, C$_{3-7}$-cycloalkyl, or C$_{3-7}$-cycloalkyl-C$_{1-4}$-alkyl, or phenyl-C$_{1-4}$-alkyl, or thienylmethyl, each of which is optionally substituted by one or more substituents independently selected from the group consisting of halogen, hydroxyl, SO$_3$H, cyano, nitro, amino, di-C$_{1-4}$-alkylamino, C$_{1-4}$-alkoxy, and C$_{1-4}$-alkyl.

10. The composition according to claim 6, wherein in the cyclic depsipeptide of formula (I):

| R¹ is: | R² is: | R³ is: | R⁴ is: | R⁵ is: | R⁶ is: |
|---|---|---|---|---|---|
| —CHMeCH₂Me | —Cyclohexyl | —CHMeCH₂Me | —Me | —CHMeCH₂Me | —Me |
| —CHMeCH₂Me | —Cyclohexyl | —CHMeCH₂Me | —Me | —CHMeCH₂Me | —Cyclohexyl |
| —CHMeCH₂Me | —CH₂—Phe | —CHMeCH₂Me | —Me | —CHMeCH₂Me | —Me |
| —CHMeCH₂Me | —CH₂—Phe | —CHMeCH₂Me | —Me | —CHMeCH₂Me | —CH₂—Phe |
| —CHMeCH₂Me | —(CH₂)₃—Me | —CHMeCH₂Me | —Me | —CHMeCH₂Me | —Me |
| —CHMeCH₂Me | —(CH₂)₃—Me | —CHMeCH₂Me | —Me | —CHMeCH₂Me | —(CH₂)₃—Me |
| —CHMe₂ | —CH₂—Phe | —CHMeCH₂Me | —Me | —CHMeCH₂Me | —Me |
| —CH₂—Phe | —CHMe₂ | —CH₂—Phe | —CHMe₂ | —CHMeCH₂Me | —CHMe₂ |
| —CH₂CHMe₂ | —CH₂—Phe | —CH₂CHMe₂ | —Me | —CH₂CHMe₂ | —CH₂—Phe |
| —(CH₂)₃—Me | —Me | —CHMeCH₂Me | —Me | —CHMeCH₂Me | —Me |
| —CHMe₂ | —Me | —CHMe₂ | —Me | —CHMe₂ | —Me |
| —CH₂—Me | —Me | —CH₂—Me | —Me | —CH₂—Me | —Me |
| —(CH₂)₂—Me | —Me | —(CH₂)₂—Me | —Me | —(CH₂)₂—Me | —Me |
| —(CH₂)₃—Me | —Me | —(CH₂)₃—Me | —Me | —(CH₂)₃—Me | —Me |
| —CH₂—CH=CH₂ | —Me | —CH₂—CH=CH₂ | —Me | —(CH₂)—CH=CH₂ | —Me |
| —CHMeCH₂Me | —Me | —CHMeCH₂Me | —Me | —CHMeCH₂Me | —CH₂—Me |
| —CHMeCH₂Me | —Me | —CHMeCH₂Me | —Me | —CHMeCH₂Me | —(CH₂)₂—Me |
| —CHMeCH₂Me | —Me | —CHMeCH₂Me | —Me | —CHMeCH₂Me | —(CH₂)₃—Me |
| —CHMeCH₂Me | —Me | —CHMeCH₂Me | —Me | —CH₂Me | —Me |
| —CHMeCH₂Me | —Me | —CHMeCH₂Me | —Me | —(CH₂)₂—Me | —Me |
| —Cyclohexyl | —Me | —Cyclohexyl | —Me | —Cyclohexyl | —Me |
| —CH₂CHMe₂ | —Cyclohexyl | —CH₂CHMe₂ | —Me | —CH₂CHMe₂ | —Cyclohexyl |
| —CH₂CHMe₂ | —Cyclohexyl | —CH₂CHMe₂ | —Me | —CH₂CHMe₂ | —Me |
| —CHMeCH₂Me | —CHMe₂ | —CHMeCH₂Me | —CHMe₂ | —CHMeCH₂Me | —Me |
| —CH₂—Phe | —Me | —CH₂—Phe | —Me | —CH₂—Phe | —Me |
| —Cyclohexyl | —Me | —Cyclohexyl | —Me | —Cyclohexyl | —Me |
| —CHMe₂ | —CHMe₂ | —CHMe₂ | —Me | —CHMe₂ | —Me |
| —CHMe₂ | —CHMe₂ | —CHMe₂ | —CHMe₂ | —CHMe₂ | —Me |
| —CH₂—Me | —CHMe₂ | —CH₂Me | —Me | —CH₂—Me | —Me |
| —CH₂—Me | —CHMe₂ | —CH₂Me | —CHMe₂ | —CH₂—Me | —Me |
| —(CH₂)₂—Me | —CHMe₂ | —(CH₂)₂—Me | —Me | —(CH₂)₂—Me | —Me |
| —(CH₂)₂—Me | —CHMe₂ | —(CH₂)₂—Me | —CHMe₂ | —(CH₂)₂—Me | —Me |
| —(CH₂)₃—Me | —CHMe₂ | —(CH₂)₃—Me | —Me | —(CH₂)₃—Me | —Me |
| —(CH₂)₃—Me | —CHMe₂ | —(CH₂)₃—Me | —CHMe₂ | —(CH₂)₃—Me | —Me |
| —CH₂—CH=CH₂ | —CHMe₂ | —CH₂—CH=CH₂ | —Me | —CH₂—CH=CH₂ | —Me |
| —CH₂—CH=CH₂ | —CHMe₂ | —CH₂—CH=CH₂ | —CHMe₂ | —CH₂—CH=CH₂ | —Me |
| —Me | —CH₂CHMe₂ | Me | Me | —CH₂CHMe₂ | —CH₂—C₆H₄—NO₂ |
| —Me | —CH₂CHMe₂ | Me | Me | —CH₂CHMe₂ | —CH₂—C₆H₄—NH₂ |
| —Me | —CH₂CHMe₂ | Me | Me | —CH₂CHMe₂ | —CH₂—C₆H₄—NMe₂ |
| —Me | —CH₂CHMe₂ | Me | Me | —CH₂CHMe₂ | —CH₂—C₆H₄—SO₃H |
| —Me | —CH₂CHMe₂ | Me | Me | —CH₂CHMe₂ | —CH₂-(thienyl) | wherein

Me represents methyl; and

Phe represents phenyl.

11. A process for preparing an endoparasiticidal composition according to claim 6 comprising mixing said cyclic depsipeptide of the formula (I) with a pharmaceutically acceptable carrier.

12. The process according to claim 11, wherein said pharmaceutically acceptable carrier comprises an extender and/or a surfactant.

13. A cyclic depsipeptide of the formula (I):

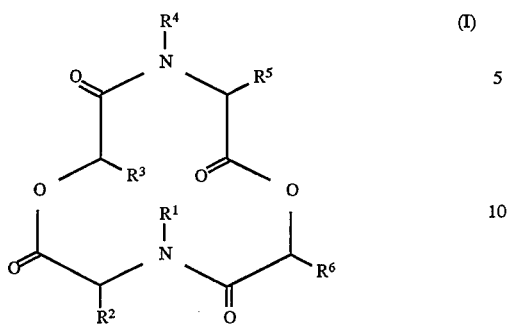

in which

R$^1$ represents hydrogen or represents C$_{1-9}$-alkyl, C$_{3-6}$-cycloalkyl, C$_{1-8}$-halogenoalkyl, aralkyl, aryl, heteroaryl, or heteroarylalkyl, each of which is optionally substituted by one or more substituents;

R$^2$, R$^3$ and R$^5$ independently of one another represent hydrogen, straight-chain or branched alkyl having up to 8 carbon atoms, halogenoalkyl, hydroxyalkyl, alkanoyloxyalkyl, alkoxyalkyl, aryloxyalkyl, mercaptoalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, or guanidinoalkyl which is optionally substituted by one or two benzyloxycarbonyl radicals or by one, two, three or four alkyl radicals, or alkoxycarbonylaminoalkyl, 9-fluorenylmethoxycarbonyl(Fmoc)aminoalkyl, alkenyl, cycloalkyl, or cycloalkylalkyl, or represent aryl, arylalkyl, heteroaryl or heteroarylalkyl, each of which is optionally substituted by one or more substituents;

R$^4$ represents C$_{1-9}$-alkyl, C$_{3-6}$-cycloalkyl, C$_{1-8}$-halogenoalkyl, aralkyl, aryl, heteroaryl, or heteroarylalkyl, each of which is optionally substituted by one or more substituents;

R$^6$ represents halogenoalkyl, hydroxyalkyl, alkanoyloxyalkyl, alkoxyalkyl, aryloxyalkyl, mercaptoalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, or guanidinoalkyl which is optionally substituted by one or two benzyloxycarbonyl radicals or by one, two, three or four alkyl radicals, or alkoxycarbonylaminoalkyl, 9-fluorenylmethoxycarbonyl(Fmoc)aminoalkyl, alkenyl, cycloalkyl, or cycloalkylalkyl, or represents aryl, arylalkyl, heteroaryl or heteroarylalkyl, each of which is optionally substituted by one or more substituents;

wherein, except as otherwise indicated, the substituents for R$^{1-6}$ are identical or different and are selected from the group consisting of alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, the halogen atoms being identical or different, hydroxyl, halogen, cyano, nitro, amino, monoalkyl- and dialkylamino having 1 to 4 carbon atoms per alkyl group, acyl radicals, alkylsulphinyl having 1 to 4 carbon atoms, halogenalkylsulphinyl having 1 to 4 carbon atoms and 1 to 5 halogen atoms, the halogen atoms being identical or different, SO$_3$H, alkylsulphonyl having 1 to 4 carbon atoms, halogenoalkylsulphonyl having 1 to 4 carbon atoms and 1 to 5 halogen atoms, arylsulphonyl having 6 or 10 aryl carbon atoms, aryl, aryloxy, heteroaryl, heteroaryloxy, each of which can have one of the aforementioned substituents, and the forminino radical (—CH=N—O-alkyl);

and with the proviso that, in the event that one of the radicals R$^1$ and R$^4$ represents a radical other than a methyl radical, then, in addition to the abovementioned possibilites, R$^6$ can represent hydrogen or straight-chain or branched C$_{1-9}$-alkyl;

or an optical isomer thereof or a racemic mixture thereof.

14. The compound according to claim 13, wherein:

R$^1$ represents hydrogen, or straight-chain or branched C$_{1-8}$-alkyl, 1–5-halogen-C$_{1-4}$-alkyl, hydroxy-C$_{1-6}$-alkyl, C$_{1-4}$-alkanoyloxy-C$_{1-6}$-alkyl, C$_{1-4}$-alkoxy-C$_{1-6}$-alkyl, aryl-C$_{1-4}$-alkyloxy-C$_{1-6}$-alkyl, mercapto-C$_{1-6}$-alkyl, C$_{1-4}$-alkylthio-C$_{1-6}$-alkyl, C$_{1-4}$-alkylsulphinyl-C$_{1-6}$-alkyl, C$_{1-4}$-alkylsulphonyl-C$_{1-6}$-alkyl, carboxy-C$_{1-6}$-alkyl, C$_{1-4}$-alkoxycarbonyl-C$_{1-6}$-alkyl, aryl-C$_{1-4}$-alkoxycarbonyl-C$_{1-6}$-alkyl, carbamoyl-C$_{1-6}$-alkyl, amino-C$_{1-6}$-alkyl, C$_{1-4}$-alkylamino-C$_{1-6}$-alkyl, di-C$_{1-4}$-alkylamino-C$_{1-6}$-alkyl, guanidino-C$_{1-6}$-alkyl, C$_{1-4}$-alkoxycarbonylamino-C$_{1-6}$-alkyl, 9-fluorenylmethoxycarbonyl(Fmoc)amino-C$_{1-6}$-alkyl, C$_{3-7}$-cycloalkyl, C$_{3-7}$-cycloalkyl -C$_{1-4}$-alkyl, phenyl, or phenyl-C$_{1-4}$-alkyl, each of which is optionally substituted by one or more substituents independently selected from the group consisting of halogen, hydroxyl, nitro, cyano, C$_{1-4}$-alkoxy, and C$_{1-4}$-alkyl;

R$^2$, R$^3$, and R$^5$ independently of one another represent hydrogen, straight-chain or branched C$_{1-8}$-alkyl, 1–5-halogen-C$_{1-4}$-alkyl, hydroxy-C$_{1-6}$-alkyl, C$_{1-4}$-alkanoyloxy-C$_{1-6}$-alkyl, C$_{1-4}$-alkoxy-C$_{1-6}$-alkyl, aryl-C$_{1-4}$-alkyloxy-C$_{1-6}$-alkyl, mercapto-C$_{1-6}$-alkyl, C$_{1-4}$-alkylthio-C$_{1-6}$-alkyl, C$_{1-4}$-alkylsulphinyl-C$_{1-6}$-alkyl, C$_{1-4}$-alkylsulphonyl-C$_{1-6}$-alkyl, carboxy-C$_{1-6}$-alkyl, C$_{1-4}$-alkoxycarbonyl-C$_{1-6}$-alkyl, aryl-C$_{1-4}$-alkoxycarbonyl-C$_{1-6}$-alkyl, carbamoyl-C$_{1-6}$-alkyl, amino-C$_{1-6}$-alkyl, C$_{1-4}$-alkylamino-C$_{1-6}$-alkyl, di-C$_{1-4}$-alkylamino-C$_{1-6}$-alkyl, C$_{2-8}$-alkenyl, C$_{3-7}$-cycloalkyl, or C$_{3-7}$-cycloalkyl-C$_{1-4}$-alkyl, or phenyl, phenyl-C$_{1-4}$-alkyl, thienylmethyl, or pyridylmethyl, each of which is optionally substituted by one or more substituents independently selected from the group consisting of halogen, hydroxyl, SO$_3$H, cyano, nitro, amino, di-C$_{1-4}$-alkylamino, C$_{1-4}$-alkoxy, and C$_{1-4}$-alkyl;

R$^4$ represents straight-chain or branched C$_{1-8}$-alkyl, 1–5-halogen-C$_{1-4}$-alkyl, hydroxy-C$_{1-6}$-alkyl, C$_{1-4}$-alkanoyloxy-C$_{1-6}$-alkyl, C$_{1-4}$-alkoxy-C$_{1-6}$-alkyl, aryl-C$_{1-4}$-alkyloxy-C$_{1-6}$-alkyl, mercapto-C$_{1-6}$-alkyl, C$_{1-4}$-alkylthio-C$_{1-6}$-alkyl, C$_{1-4}$-alkylsulphinyl-C$_{1-6}$-alkyl, C$_{1-4}$-alkylsulphonyl-C$_{1-6}$-alkyl, carboxy-C$_{1-6}$-alkyl, C$_{1-4}$-alkoxycarbonyl-C$_{1-6}$-alkyl, aryl-C$_{1-4}$-alkoxycarbonyl-C$_{1-6}$-alkyl, carbamoyl-C$_{1-6}$-alkyl, amino-C$_{1-6}$-alkyl, C$_{1-4}$-alkylamino-C$_{1-6}$-alkyl, di-C$_{1-4}$-alkylamino-C$_{1-6}$-alkyl, guanidino-C$_{1-6}$-alkyl, C$_{1-4}$-alkoxycarbonylamino-C$_{1-6}$-alkyl, 9-fluorenylmethoxycarbonyl(Fmoc)amino-C$_{1-6}$-alkyl, C$_{3-7}$-cycloalkyl, C$_{3-7}$-cycloalkyl-C$_{1-4}$-alkyl, phenyl, or phenyl-C$_{1-4}$-alkyl, each of which is optionally substituted by one or more substituents independently selected from the group consisting of halogen, hydroxyl, nitro, cyano, C$_{1-4}$-alkoxy, and C$_{1-4}$-alkyl;

$R^6$ represents 1-5-halogen-$C_{1-4}$-alkyl, hydroxy-$C_{1-6}$-alkyl, $C_{1-4}$-alkanoyloxy-$C_{1-6}$-alkyl, $C_{1-4}$-alkoxy-$C_{1-6}$-alkyl, aryl-$C_{1-4}$-alkyloxy-$C_{1-6}$-alkyl, mercapto-$C_{1-6}$-alkyl, $C_{1-4}$-alkylthio-$C_{1-6}$-alkyl, $C_{1-4}$-alkylsulphinyl-$C_{1-6}$-alkyl, $C_{1-4}$-alkylsulphonyl-$C_{1-6}$-alkyl, carboxy-$C_{1-6}$-alkyl, $C_{1-4}$-alkoxycarbonyl-$C_{1-6}$-alkyl, aryl-$C_{1-4}$-alkoxycarbonyl-$C_{1-6}$-alkyl, carbamoyl-$C_{1-6}$-alkyl, amino-$C_{1-6}$-alkyl, $C_{1-4}$-alkylamino-$C_{1-6}$-alkyl, di-$C_{1-4}$-alkylamino-$C_{1-6}$-alkyl, $C_{2-8}$-alkenyl, $C_{3-7}$-cycloalkyl, or $C_{3-7}$-cycloalkyl-$C_{1-4}$-alkyl, or phenyl, phenyl-$C_{1-4}$-alkyl, thienylmethyl, or pyridylmethyl, each of which is optionally substituted by one or more substituents independently selected from the group consisting of halogen, hydroxyl, $SO_3H$, cyano, nitro, amino, di-$C_{1-4}$-alkylamino, $C_{1-4}$-alkoxy, and $C_{1-4}$-alkyl;

with the proviso that, in the event that one of the radicals $R^1$ and $R^4$ represents a radical other than a methyl radical, then, in addition to the abovementioned possibilites, $R^6$ can represent hydrogen or straight-chain or branched $C_{1-9}$-alkyl;

or an optical isomer thereof or a racemic mixture thereof.

15. The compound according to claim 13, wherein:

$R^1$ represents hydrogen, or straight-chain or branched $C_{1-8}$-alkyl, 1-5-halogen-$C_{1-4}$-alkyl, hydroxy-$C_{1-6}$-alkyl, $C_{1-4}$-alkanoyloxy-$C_{1-6}$-alkyl, $C_{1-4}$-alkoxy-$C_{1-6}$-alkyl, aryl-$C_{1-4}$-alkyloxy-$C_{1-6}$-alkyl, $C_{1-4}$-alkoxycarbonylamino-$C_{1-6}$-alkyl, $C_{3-7}$-cycloalkyl, $C_{3-7}$-cycloalkyl-$C_{1-4}$-alkyl, or phenyl-$C_{1-4}$-alkyl, each of which is optionally substituted by one or more substituents independently selected from the group consisting of halogen, hydroxyl, nitro, cyano, $C_{1-4}$-alkoxy, and $C_{1-4}$-alkyl;

$R^2$, $R^3$, and $R^5$ independently of one another represent hydrogen, straight-chain or branched $C_{1-8}$-alkyl, 1-5-halogen-$C_{1-4}$-alkyl, hydroxy-$C_{1-6}$-alkyl, aryl-$C_{1-4}$-alkyloxy-$C_{1-6}$-alkyl, carboxy-$C_{1-6}$-alkyl, $C_{1-4}$-alkoxycarbonyl-$C_{1-6}$-alkyl, aryl-$C_{1-4}$-alkoxycarbonyl-$C_{1-6}$-alkyl, $C_{1-4}$-alkylamino-$C_{1-6}$-alkyl, di-$C_{1-4}$-alkylamino-$C_{1-6}$-alkyl, $C_{2-8}$-alkenyl, $C_{3-7}$-cycloalkyl, or $C_{3-7}$-cycloalkyl-$C_{1-4}$-alkyl, or phenyl, phenyl-$C_{1-4}$-alkyl, or thienylmethyl, each of which is optionally substituted by one or more substituents independently selected from the group consisting of halogen, hydroxyl, $SO_3H$, cyano, nitro, amino, di-$C_{1-4}$-alkylamino, $C_{1-4}$-alkoxy, and $C_{1-4}$-alkyl;

$R^4$ represents straight-chain or branched $C_{1-8}$-alkyl, 1-5-halogen-$C_{1-4}$-alkyl, hydroxy-$C_{1-6}$-alkyl, $C_{1-4}$-alkanoyloxy-$C_{1-6}$-alkyl, $C_{1-4}$-alkoxy-$C_{1-6}$-alkyl, aryl-$C_{1-4}$-alkyloxy-$C_{1-6}$-alkyl, $C_{1-4}$-alkoxycarbonylamino-$C_{1-6}$-alkyl, $C_{3-7}$-cycloalkyl, $C_{3-7}$-cycloalkyl-$C_{1-4}$-alkyl, or phenyl-$C_{1-4}$-alkyl, each of which is optionally substituted by one or more substituents independently selected from the group consisting of halogen, hydroxyl, nitro, cyano, $C_{1-4}$-alkoxy, and $C_{1-4}$-alkyl;

$R^6$ represents 1-5-halogen-$C_{1-4}$-alkyl, hydroxy-$C_{1-6}$-alkyl aryl-$C_{1-4}$-alkyloxy-$C_{1-6}$-alkyl, carboxy-$C_{1-6}$-alkyl, $C_{1-4}$-alkoxycarbonyl-$C_{1-6}$-alkyl, aryl-$C_{1-4}$-alkoxycarbonyl-$C_{1-6}$-alkyl, $C_{1-4}$-alkylamino-$C_{1-6}$-alkyl, di-$C_{1-4}$-alkylamino-$C_{1-6}$-alkyl, $C_{2-8}$-alkenyl, $C_{3-7}$-cycloalkyl, or $C_{3-7}$-cycloalkyl-$C_{1-4}$-alkyl, or phenyl, phenyl-$C_{1-4}$-alkyl, or thienylmethyl, each of which is optionally substituted by one or more substituents independently selected from the group consisting of halogen, hydroxyl, $SO_3H$, cyano, nitro, amino, di-$C_{1-4}$-alkylamino, $C_{1-4}$-alkoxy, and $C_{1-4}$-alkyl;

with the proviso that, in the event that one of the radicals $R^1$ and $R^4$ represents a radical other than a methyl radical, then, in addition to the abovementioned possibilites, $R^6$ can represent hydrogen or straight-chain or branched $C_{1-9}$-alkyl;

or an optical isomer thereof or a racemic mixture thereof.

16. The compound according to claim 13, wherein:

$R^1$ represents hydrogen, or straight-chain or branched $C_{1-8}$-alkyl, $C_{3-7}$-cycloalkyl-$C_{1-4}$-alkyl, or phenyl-$C_{1-4}$-alkyl;

$R^2$, $R^3$, and $R^5$ represent hydrogen, straight-chain or branched $C_{1-8}$-alkyl, 1-5-halogen-$C_{1-4}$-alkyl, $C_{2-8}$-alkenyl, $C_{3-7}$-cycloalkyl, or $C_{3-7}$-cycloalkyl-$C_{1-4}$-alkyl, or phenyl-$C_{1-4}$-alkyl, or thienylmethyl, each of which is optionally substituted by one or more substituents independently selected from the group consisting of halogen, hydroxyl, $SO_3H$, cyano, nitro, amino, di-$C_{1-4}$-alkylamino, $C_{1-4}$-alkoxy, and $C_{1-4}$-alkyl;

$R^4$ represents straight-chain or branched $C_{1-8}$-alkyl, $C_{3-7}$-cycloalkyl-$C_{1-4}$-alkyl, or phenyl-$C_{1-4}$-alkyl;

$R^6$ represents 1-5-halogen-$C_{1-4}$-alkyl, $C_{2-8}$-alkenyl, $C_{3-7}$-cycloalkyl, or $C_{3-7}$-cycloalkyl-$C_{1-4}$-alkyl, or phenyl-$C_{1-4}$-alkyl, or thienylmethyl, each of which is optionally substituted by one or more substituents independently selected from the group consisting of halogen, hydroxyl, $SO_3H$, cyano, nitro, amino, di-$C_{1-4}$-alkylamino, $C_{1-4}$-alkoxy, and $C_{1-4}$-alkyl;

with the proviso that, in the event that one of the radicals $R^1$ and $R^4$ represents a radical other than a methyl radical, then, in addition to the abovementioned possibilites, $R^6$ can represent hydrogen or straight-chain or branched $C_{1-9}$-alkyl;

or an optical isomer thereof or a racemic mixture thereof.

17. The compound according to claim 13, wherein:

| $R^1$ is: | $R^2$ is: | $R^3$ is: | $R^4$ is: | $R^5$ is: | $R^6$ is: |
| --- | --- | --- | --- | --- | --- |
| —CHMeCH$_2$Me | —Cyclohexyl | —CHMeCH$_2$Me | —Me | —CHMeCH$_2$Me | —Me |
| —CHMeCH$_2$Me | —Cyclohexyl | —CHMeCH$_2$Me | —Me | —CHMeCH$_2$Me | —Cyclohexyl |
| —CHMeCH$_2$Me | —CH$_2$—Phe | —CHMeCH$_2$Me | —Me | —CHMeCH$_2$Me | —Me |
| —CHMeCH$_2$Me | —CH$_2$—Phe | —CHMeCH$_2$Me | —Me | —CHMeCH$_2$Me | —CH$_2$—Phe |
| —CHMeCH$_2$Me | —(CH$_2$)$_3$—Me | —CHMeCH$_2$Me | —Me | —CHMeCH$_2$Me | —Me |
| —CHMeCH$_2$Me | —(CH$_2$)$_3$—Me | —CHMeCH$_2$Me | —Me | —CHMeCH$_2$Me | —(CH$_2$)$_3$—Me |
| —CHMe$_2$ | —CH$_2$—Phe | —CHMeCH$_2$Me | —Me | —CHMeCH$_2$Me | —Me |
| —CH$_2$—Phe | —CHMe$_2$ | —CH$_2$—Phe | —CHMe$_2$ | —CHMeCH$_2$Me | —CHMe$_2$ |
| —CH$_2$CHMe$_2$ | —CH$_2$—Phe | —CH$_2$CHMe$_2$ | —Me | —CH$_2$CHMe$_2$ | —CH$_2$—Phe |
| —(CH$_2$)$_3$—Me | —Me | —CHMeCH$_2$Me | —Me | —CHMeCH$_2$Me | —Me |
| —CHMe$_2$ | —Me | —CHMe$_2$ | —Me | —CHMe$_2$ | —Me |
| —CH$_2$—Me | —Me | —CH$_2$—Me | —Me | —CH$_2$—Me | —Me |
| —(CH$_2$)$_2$—Me | —Me | —(CH$_2$)$_2$—Me | —Me | —(CH$_2$)$_2$—Me | —Me |

-continued

| R¹ is: | R² is: | R³ is: | R⁴ is: | R⁵ is: | R⁶ is: |
|---|---|---|---|---|---|
| —(CH₂)₃—Me | —Me | —(CH₂)₃—Me | —Me | —(CH₂)₃—Me | —Me |
| —CH₂—CH=CH₂ | —Me | —CH₂—CH=CH₂ | —Me | —(CH₂)—CH=CH₂ | —Me |
| —CHMeCH₂Me | —Me | —CHMeCH₂Me | —Me | —CHMeCH₂Me | —CH₂—Me |
| —CHMeCH₂Me | —Me | —CHMeCH₂Me | —Me | —CHMeCH₂Me | —(CH₂)₂—Me |
| —CHMeCH₂Me | —Me | —CHMeCH₂Me | —Me | —CHMeCH₂Me | —(CH₂)₃—Me |
| —CHMeCH₂Me | —Me | —CHMeCH₂Me | —Me | —CH₂Me | —Me |
| —CHMeCH₂Me | —Me | —CHMeCH₂Me | —Me | —(CH₂)₂—Me | —Me |
| —Cyclohexyl | —Me | —Cyclohexyl | —Me | —Cyclohexyl | —Me |
| —CH₂CHMe₂ | —Cyclohexyl | —CH₂CHMe₂ | —Me | —CH₂CHMe₂ | —Cyclohexyl |
| —CH₂CHMe₂ | —Cyclohexyl | —CH₂CHMe₂ | —Me | —CH₂CHMe₂ | —Me |
| —CHMeCH₂Me | —CHMe₂ | —CHMeCH₂Me | —CHMe₂ | —CHMeCH₂Me | —Me |
| —CH₂—Phe | —Me | —CH₂—Phe | —Me | —CH₂—Phe | —Me |
| —Cyclohexyl | —Me | —Cyclohexyl | —Me | —Cyclohexyl | —Me |
| —CHMe₂ | —CHMe₂ | —CHMe₂ | —Me | —CHMe₂ | —Me |
| —CHMe₂ | —CHMe₂ | —CHMe₂ | —CHMe₂ | —CHMe₂ | —Me |
| —CH₂—Me | —CHMe₂ | —CH₂Me | —Me | —CH₂—Me | —Me |
| —CH₂—Me | —CHMe₂ | —CH₂Me | —CHMe₂ | —CH₂—Me | —Me |
| —(CH₂)₂—Me | —CHMe₂ | —(CH₂)₂—Me | —Me | —(CH₂)₂—Me | —Me |
| —(CH₂)₂—Me | —CHMe₂ | —(CH₂)₂—Me | —CHMe₂ | —(CH₂)₂—Me | —Me |
| —(CH₂)₃—Me | —CHMe₂ | —(CH₂)₃—Me | —Me | —(CH₂)₃—Me | —Me |
| —(CH₂)₃—Me | —CHMe₂ | —(CH₂)₃—Me | —CHMe₂ | —(CH₂)₃—Me | —Me |
| —CH₂—CH=CH₂ | —CHMe₂ | —CH₂—CH=CH₂ | —Me | —CH₂—CH=CH₂ | —Me |
| —CH₂—CH=CH₂ | —CHMe₂ | —CH₂—CH=CH₂ | —CHMe₂ | —CH₂—CH=CH₂ | —Me |
| —Me | —CH₂CHMe₂ | Me | Me | —CH₂CHMe₂ | —CH₂—C₆H₄—NO₂ |
| —Me | —CH₂CHMe₂ | Me | Me | —CH₂CHMe₂ | —CH₂—C₆H₄—NH₂ |
| —Me | —CH₂CHMe₂ | Me | Me | —CH₂CHMe₂ | —CH₂—C₆H₄—NMe₂ |
| —Me | —CH₂CHMe₂ | Me | Me | —CH₂CHMe₂ | —CH₂—C₆H₄—SO₃H |
| —Me | —CH₂CHMe₂ | Me | Me | —CH₂CHMe₂ | —CH₂—(2-thienyl) | wherein

Me represents methyl; and

Phe represents phenyl.